(12) United States Patent
Lan et al.

(10) Patent No.: US 10,071,147 B2
(45) Date of Patent: *Sep. 11, 2018

(54) METHOD FOR ENHANCING IMMUNE RESPONSE IN THE TREATMENT OF INFECTIOUS AND MALIGNANT DISEASES

(71) Applicant: Taipei Veterans General Hospital, Taipei (TW)

(72) Inventors: Keng-Li Lan, Taipei (TW); Yi-Sheng Shih, Taipei (TW); Keng-Hsin Lan, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 172 days.

This patent is subject to a terminal disclaimer.

(21) Appl. No.: 15/044,613

(22) Filed: Feb. 16, 2016

(65) Prior Publication Data

US 2017/0028040 A1 Feb. 2, 2017

Related U.S. Application Data

(62) Division of application No. 14/079,088, filed on Nov. 13, 2013, now Pat. No. 9,289,480, which is a division of application No. 13/532,460, filed on Jun. 25, 2012, now Pat. No. 8,609,625.

(60) Provisional application No. 61/500,825, filed on Jun. 24, 2011.

(51) Int. Cl.
| | | |
|---|---|---|
| A61K 31/713 | (2006.01) |
| A61K 38/17 | (2006.01) |
| A61K 39/00 | (2006.01) |
| A61K 48/00 | (2006.01) |
| C07H 21/04 | (2006.01) |
| C07K 14/705 | (2006.01) |
| A61K 45/06 | (2006.01) |

(52) U.S. Cl.
CPC ...... *A61K 39/0011* (2013.01); *A61K 38/1774* (2013.01); *A61K 45/06* (2013.01); *A61K 2039/53* (2013.01); *A61K 2039/55533* (2013.01); *A61K 2039/55555* (2013.01); *A61K 2039/572* (2013.01); *A61K 2039/6031* (2013.01)

(58) Field of Classification Search
None
See application file for complete search history.

(56) References Cited

U.S. PATENT DOCUMENTS

| | | | | |
|---|---|---|---|---|
| 8,609,625 B2 * | 12/2013 | Lan | .......... | A61K 39/0011 514/44 R |
| 9,289,480 B2 * | 3/2016 | Lan | .......... | A61K 39/0011 |

* cited by examiner

*Primary Examiner* — Ilia I Ouspenski
(74) *Attorney, Agent, or Firm* — WPAT, PC

(57) ABSTRACT

The present invention pertains to a new approach for the treatment of infectious and malignant diseases. The present invention provides new DNA and protein vaccines for the treatment of infectious and malignant diseases through enhancing immune response.

4 Claims, 35 Drawing Sheets
Specification includes a Sequence Listing.

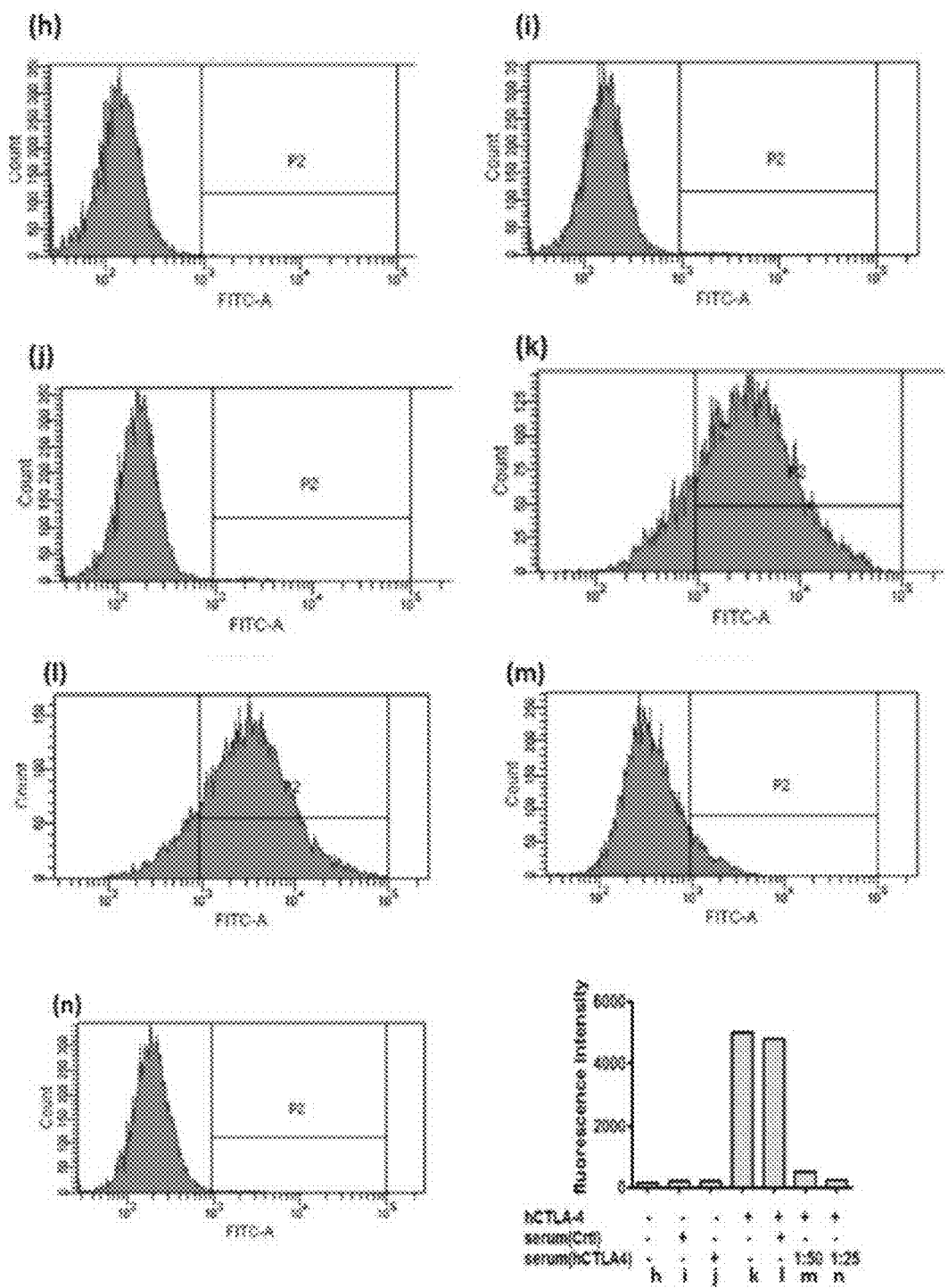
Figure 9-Cont.

(a) Constructs of membrane-tethered proteins (with PLAP domain)

IL2 signal sequence ("IL2ss")

transmembrane domain sequence of placental alkaline phosphatase (PLAP)

(b) Constructs of secreted proteins (without PLAP domain)

IL2 signal sequence ("IL2ss")

SEQUENCE LISTING

```
<160> NUMBER OF SEQ ID NOS: 36

<210> SEQ ID NO 1
<211> LENGTH: 549
<212> TYPE: DNA
<213> ORGANISM: Artificial Sequence
<220> FEATURE:
<223> OTHER INFORMATION: IL2ss-hCTLA-4-PLAP

<400> SEQUENCE: 1
atgtatagga tgcaactgct gtcttgcatt gctctgtctc tggcactggt cactaactct      60
gccaggatcc tggcaatgca cgtggcccag cctgctgtgg tactggccag cagccgaggc     120
atcgccagct ttgtgtgtga gtatgcatct ccaggcaaag ccactgaggt ccgggtgaca     180
gtgcttcggc aggctgacag ccaggtgact gaagtctgtg cggcaaccta catgatgggg     240
aatgagttga ccttcctaga tgattccatc tgcacgggca cctccagtgg aaatcaagtg     300
aacctcacta tccaaggact gagggccatg gacacgggac tctacatctg caaggtggag     360
ctcatgtacc caccgccata ctacctgggc ataggcaacg gaacccagat ttatgtaatt     420
gatccagaac cgtgcccaga ttctgaattc accactgatg ctgcccatcc tggaaggtct     480
gtggtgcctg ccttgctgcc tctgctggct ggcactctgc tgctgctgga gactgccact     540
gctccctaa                                                            549

<210> SEQ ID NO 2
<211> LENGTH: 564
<212> TYPE: DNA
<213> ORGANISM: Artificial Sequence
<220> FEATURE:
<223> OTHER INFORMATION: IL2ss-mCTLA-4-PLAP

<400> SEQUENCE: 2
atgtatagga tgcaactgct gtcttgcatt gctctgtctc tggcactggt cactaactct      60
gccaggatcc tgaattcat ggaagccata caggtgaccc aaccttcagt ggtgttggct     120
agcagccatg gtgtcgccag ctttccatgt gaatattcac cgtcacacaa cactgatgag     180
gtccgggtga ctgtgctgcg gcagacaaat gaccaaatga ctgaggtctg tgccacgaca     240
ttcacagaga agaatacagt gggcttccta gattacccct ctgcagtgg taccttttaat     300 gaaagcagag tgaacctcac catccaagga ctgagagctg ttgacacggg actgtacctc     360
tgcaaggtgg aactcatgta cccaccgcca tactttgtgg gcatgggcaa cgggacgcag     420
atttatgtca ttgatccaga accatgcccg gattctgacc aattcaccac tgatgctgcc     480
catcctggaa ggtctgtggt gcctgccttg ctgcctctgc tggctggcac tctgctgctg     540
ctggagactg ccactgctcc ctaa                                           564
```

<210> SEQ ID NO 3
<211> LENGTH: 627
<212> TYPE: DNA
<213> ORGANISM: Artificial Sequence
<220> FEATURE:
<223> OTHER INFORMATION: IL2ss-hPD-1-PLAP

<400> SEQUENCE: 3

```
atgtatagga tgcaactgct gtcttgcatt gctctgtctc tggcactggt cactaactct    60
gccaggatcc tgccaggatg gttcttagac tccccagaca ggccctggaa ccccccacc   120
ttctccccag ccctgctcgt ggtgaccgaa ggggacaacg ccaccttcac ctgcagcttc   180
tccaacacat cggagagctt cgtgctaaac tggtaccgca tgagcccag caaccagacg    240
gacaagctgg ccgccttccc cgaggaccgc agccagcccg ccaggactg ccgcttccgt     300
gtcacacaac tgcccaacgg cgtgacttc acatgagcg tggtcagggc cggcgcaat      360
gacagcggca cctacctctg tgggccatc tccctggccc caaggcgca gatcaaagag      420
agcctgcggg cagagctcag ggtgacagag agaagggcag aagtgcccac agcccacccc   480
agcccctcac ccaggccagc cggccagttc caaaccctgg tggaattcac cactgatgct   540
gcccatcctg aaggtctgt ggtgcctgcc ttgctgcctc tgctggctgg cactctgctg     600
ctgctggaga ctgccactgc tccctaa                                         627
```

<210> SEQ ID NO 4
<211> LENGTH: 525
<212> TYPE: DNA
<213> ORGANISM: Artificial Sequence
<220> FEATURE:
<223> OTHER INFORMATION: IL2ss-hPD-1

<400> SEQUENCE: 4

```
atgtatagga tgcaactgct gtcttgcatt gctctgtctc tggcactggt cactaactct    60
gccaggatcc tgccaggatg gttcttagac tccccagaca ggccctggaa ccccccacc   120
ttctccccag ccctgctcgt ggtgaccgaa ggggacaacg ccaccttcac ctgcagcttc   180
tccaacacat cggagagctt cgtgctaaac tggtaccgca tgagcccag caaccagacg    240
gacaagctgg ccgccttccc cgaggaccgc agccagcccg ccaggactg ccgcttccgt     300
gtcacacaac tgcccaacgg cgtgacttc acatgagcg tggtcagggc cggcgcaat      360
gacagcggca cctacctctg tgggccatc tccctggccc caaggcgca gatcaaagag      420
agcctgcggg cagagctcag ggtgacagag agaagggcag aagtgcccac agcccacccc   480
agcccctcac ccaggccagc cggccagttc caaaccctgg tgtaa                    525
```

<210> SEQ ID NO 5
<211> LENGTH: 837
<212> TYPE: DNA
<213> ORGANISM: Artificial Sequence
<220> FEATURE:
<223> OTHER INFORMATION: IL2ss hPD-L1-PLAP

<400> SEQUENCE: 5

```
atgtatagga tgcaactgct gtcttgcatt gctctgtctc tggcactggt cactaactct    60
gccaggatcc tgttcactgt cacggttccc aaggacctat atgtggtaga gtatggtagc   120
aatatgacaa ttgaatgcaa attcccagta gaaaaacaat tagacctggc tgcactaatt   180
gtctattggg aaatggagga taagaacatt attcaatttg tgcatggaga ggaagacctg   240
```

| | |
|---|---|
| aaggttcagc atagtagcta cagacagagg gcccggctgt tgaaggacca gctctccctg | 300 |
| ggaaatgctg cacttcagat cacagatgtg aaattgcagg atgcaggggt gtaccgctgc | 360 |
| atgatcagct atggtggtgc cgactacaag cgaattactg tgaaagtcaa tgccccatac | 420 |
| aacaaaatca ccaaagaat tttggttgtg atccagtca cctctgaaca tgaactgaca | 480 |
| tgtcaggctg agggctaccc caaggccgaa gtcatctgga caagcagtga ccatcaagtc | 540 |
| ctgagtggta agaccaccac caccaattcc aagagagagg agaagctttt caatgtgacc | 600 |
| agcacactga aatcaacac aacaactaat gagattttct actgcacttt taggagatta | 660 |
| gatcctgagg aaaaccatac agctgaattg gtcatcccag aactacctct ggcacatcct | 720 |
| ccaaatgaaa gggaattcac cactgatgct gcccatcctg aaggtctgt ggtgcctgcc | 780 |
| ttgctgcctc tgctggctgg cactctgctg ctgctggaga ctgccactgc tccctaa | 837 |

<210> SEQ ID NO 6
<211> LENGTH: 735
<212> TYPE: DNA
<213> ORGANISM: Artificial Sequence
<220> FEATURE:
<223> OTHER INFORMATION: IL2ss-hPD-L1

<400> SEQUENCE: 6

| | |
|---|---|
| atgtatagga tgcaactgct gtcttgcatt gctctgtctc tggcactggt cactaactct | 60 |
| gccaggatcc tgttcactgt cacgttccc aaggacctat atgtggtaga gtatggtagc | 120 |
| aatatgacaa ttgaatgcaa attcccagta gaaaacaat tagacctggc tgcactaatt | 180 |
| gtctattggg aaatggagga taagaacatt attcaatttg tgcatggaga ggaagacctg | 240 |
| aaggttcagc atagtagcta cagacagagg gcccggctgt tgaaggacca gctctccctg | 300 |
| ggaaatgctg cacttcagat cacagatgtg aaattgcagg atgcaggggt gtaccgctgc | 360 |
| atgatcagct atggtggtgc cgactacaag cgaattactg tgaaagtcaa tgccccatac | 420 |
| aacaaaatca ccaaagaat tttggttgtg atccagtca cctctgaaca tgaactgaca | 480 |
| tgtcaggctg agggctaccc caaggccgaa gtcatctgga caagcagtga ccatcaagtc | 540 |
| ctgagtggta agaccaccac caccaattcc aagagagagg agaagctttt caatgtgacc | 600 |
| agcacactga aatcaacac aacaactaat gagattttct actgcacttt taggagatta | 660 |
| gatcctgagg aaaaccatac agctgaattg gtcatcccag aactacctct ggcacatcct | 720 |
| ccaaatgaaa ggtaa | 735 |

<210> SEQ ID NO 7
<211> LENGTH: 1005
<212> TYPE: DNA
<213> ORGANISM: Artificial Sequence
<220> FEATURE:
<223> OTHER INFORMATION: IL2ss-hCTLA4-hPD-1-PLAP

<400> SEQUENCE: 7

| | |
|---|---|
| atgtatagga tgcaactgct gtcttgcatt gctctgtctc tggcactggt cactaactct | 60 |
| gccaggatcc tggcaatgca cgtggcccag cctgctgtgg tactggccag cagccgaggc | 120 |
| atcgccagct ttgtgtgtga gtatgcatct ccaggcaaag ccactgaggt ccgggtgaca | 180 |
| gtgcttcggc aggctgacag ccaggtgact gaagtctgtg cggcaaccta catgatgggg | 240 |
| aatgagttga ccttcctaga tgattccatc tgcacgggca cctccagtgg aaatcaagtg | 300 |
| aacctcacta tccaaggact gagggccatg gacacgggac tctacatctg caaggtggag | 360 |
| ctcatgtacc caccgccata ctacctgggc ataggcaacg aacccagat ttatgtaatt | 420 |

-continued

```
gatccagaac cgtgcccaga ttctgaattc ccaggatggt tcttagactc cccagacagg      480
ccctggaacc cccccacctt ctccccagcc ctgctcgtgg tgaccgaagg ggacaacgcc      540
accttcacct gcagcttctc caacacatcg gagagcttcg tgctaaactg gtaccgcatg      600
agccccagca accagacgga caagctggcc gccttccccg aggaccgcag ccagcccggc      660
caggactgcc gcttccgtgt cacacaactg cccaacgggc gtgacttcca catgagcgtg      720
gtcagggccc ggcgcaatga cagcggcacc tacctctgtg gggccatctc cctggccccc      780
aaggcgcaga tcaaagagag cctgcgggca gagctcaggg tgacagagag aagggcagaa      840
gtgcccacag cccaccccag cccctcaccc aggccagccg ccagttccaa accctggtg      900 gaattcacca ctgatgctgc ccatcctgga aggtctgtgg tgcctgcctt gctgcctctg      960
ctggctggca ctctgctgct gctggagact gccactgctc cctaa                    1005

<210> SEQ ID NO 8
<211> LENGTH: 903
<212> TYPE: DNA
<213> ORGANISM: Artificial Sequence
<220> FEATURE:
<223> OTHER INFORMATION: IL2ss-hCTLA4-hPD-1

<400> SEQUENCE: 8
atgtatagga tgcaactgct gtcttgcatt gctctgtctc tggcactggt cactaactct       60
gccaggatcc tggcaatgca cgtggcccag cctgctgtgg tactggccag cagccgaggc      120
atcgccagct ttgtgtgtga gtatgcatct ccaggcaaag ccactgaggt ccgggtgaca      180
gtgcttcggc aggctgacag ccaggtgact gaagtctgtg cggcaaccta catgatgggg      240
aatgagttga ccttcctaga tgattccatc tgcacgggca cctccagtgg aaatcaagtg      300
aacctcacta tccaaggact gagggccatg gacacgggac tctacatctg caaggtggag      360
ctcatgtacc caccgccata ctacctgggc ataggcaacg gaacccagat ttatgtaatt      420
gatccagaac cgtgcccaga ttctgaattc ccaggatggt tcttagactc cccagacagg      480
ccctggaacc cccccacctt ctccccagcc ctgctcgtgg tgaccgaagg ggacaacgcc      540
accttcacct gcagcttctc caacacatcg gagagcttcg tgctaaactg gtaccgcatg      600
agccccagca accagacgga caagctggcc gccttccccg aggaccgcag ccagcccggc      660
caggactgcc gcttccgtgt cacacaactg cccaacgggc gtgacttcca catgagcgtg      720
gtcagggccc ggcgcaatga cagcggcacc tacctctgtg gggccatctc cctggccccc      780
aaggcgcaga tcaaagagag cctgcgggca gagctcaggg tgacagagag aagggcagaa      840
gtgcccacag cccaccccag cccctcaccc aggccagccg ccagttccaa accctggtg      900 taa                                                                   903

<210> SEQ ID NO 9
<211> LENGTH: 1212
<212> TYPE: DNA
<213> ORGANISM: Artificial Sequence
<220> FEATURE:
<223> OTHER INFORMATION: IL2ss-hCTLA4-hPD-L1-PLAP

<400> SEQUENCE: 9
atgtatagga tgcaactgct gtcttgcatt gctctgtctc tggcactggt cactaactct       60
gccaggatcc tggcaatgca cgtggcccag cctgctgtgg tactggccag cagccgaggc      120
atcgccagct ttgtgtgtga gtatgcatct ccaggcaaag ccactgaggt ccgggtgaca      180
```

| | |
|---|---|
| gtgcttcggc aggctgacag ccaggtgact gaagtctgtg cggcaaccta catgatgggg | 240 |
| aatgagttga ccttcctaga tgattccatc tgcacgggca cctccagtgg aaatcaagtg | 300 |
| aacctcacta tccaaggact gagggccatg gacacgggac tctacatctg caaggtggag | 360 |
| ctcatgtacc caccgccata ctacctgggc ataggcaacg gaacccagat ttatgtaatt | 420 |
| gatccagaac cgtgcccaga ttctgaattc actgtcacgg ttcccaagga cctatatgtg | 480 |
| gtagagtatg gtagcaatat gacaattgaa tgcaaattcc cagtagaaaa acaattagac | 540 |
| ctggctgcac taattgtcta ttgggaaatg gaggataaga acattattca atttgtgcat | 600 |
| ggagaggaag acctgaaggt tcagcatagt agctacagac agagggcccg gctgttgaag | 660 |
| gaccagctct ccctgggaaa tgctgcactt cagatcacag atgtgaaatt gcaggatgca | 720 |
| ggggtgtacc gctgcatgat cagctatggt ggtgccgact acaagcgaat tactgtgaaa | 780 |
| gtcaatgccc catacaacaa aatcaaccaa agaattttgg ttgtggatcc agtcacctct | 840 |
| gaacatgaac tgacatgtca ggctgagggc taccccaagg ccgaagtcat ctggacaagc | 900 |
| agtgaccatc aagtcctgag tggtaagacc accaccacca attccaagag agaggagaag | 960 |
| cttttcaatg tgaccagcac actgagaatc aacacaacaa ctaatgagat tttctactgc | 1020 |
| acttttagga gattagatcc tgaggaaaac catacagctg aattggtcat cccagaacta | 1080 |
| cctctggcac atcctccaaa tgaaagggaa ttcaccactg atgctgccca tcctggaagg | 1140 |
| tctgtggtgc ctgccttgct gcctctgctg gctggcactc tgctgctgct ggagactgcc | 1200 |
| actgctccct aa | 1212 |

<210> SEQ ID NO 10
<211> LENGTH: 1110
<212> TYPE: DNA
<213> ORGANISM: Artificial Sequence
<220> FEATURE:
<223> OTHER INFORMATION: IL2ss-hCTLA4-hPD-L1

<400> SEQUENCE: 10

| | |
|---|---|
| atgtatagga tgcaactgct gtcttgcatt gctctgtctc tggcactggt cactaactct | 60 |
| gccaggatcc tggcaatgca cgtggcccag cctgctgtgg tactggccag cagccgaggc | 120 |
| atcgccagct ttgtgtgtga gtatgcatct ccaggcaaag ccactgaggt ccgggtgaca | 180 |
| gtgcttcggc aggctgacag ccaggtgact gaagtctgtg cggcaaccta catgatgggg | 240 |
| aatgagttga ccttcctaga tgattccatc tgcacgggca cctccagtgg aaatcaagtg | 300 |
| aacctcacta tccaaggact gagggccatg gacacgggac tctacatctg caaggtggag | 360 |
| ctcatgtacc caccgccata ctacctgggc ataggcaacg gaacccagat ttatgtaatt | 420 |
| gatccagaac cgtgcccaga ttctgaattc actgtcacgg ttcccaagga cctatatgtg | 480 |
| gtagagtatg gtagcaatat gacaattgaa tgcaaattcc cagtagaaaa acaattagac | 540 |
| ctggctgcac taattgtcta ttgggaaatg gaggataaga acattattca atttgtgcat | 600 |
| ggagaggaag acctgaaggt tcagcatagt agctacagac agagggcccg gctgttgaag | 660 |
| gaccagctct ccctgggaaa tgctgcactt cagatcacag atgtgaaatt gcaggatgca | 720 |
| ggggtgtacc gctgcatgat cagctatggt ggtgccgact acaagcgaat tactgtgaaa | 780 |
| gtcaatgccc catacaacaa aatcaaccaa agaattttgg ttgtggatcc agtcacctct | 840 |
| gaacatgaac tgacatgtca ggctgagggc taccccaagg ccgaagtcat ctggacaagc | 900 |
| agtgaccatc aagtcctgag tggtaagacc accaccacca attccaagag agaggagaag | 960 |
| cttttcaatg tgaccagcac actgagaatc aacacaacaa ctaatgagat tttctactgc | 1020 |

| | |
|---|---|
| acttttagga gattagatcc tgaggaaaac catacagctg aattggtcat cccagaacta | 1080 |
| cctctggcac atcctccaaa tgaaaggtaa | 1110 |

<210> SEQ ID NO 11
<211> LENGTH: 633
<212> TYPE: DNA
<213> ORGANISM: Artificial Sequence
<220> FEATURE:
<223> OTHER INFORMATION: IL2ss-mPD-1-PLAP

<400> SEQUENCE: 11

| | |
|---|---|
| atgtatagga tgcaactgct gtcttgcatt gctctgtctc tggcactggt cactaactct | 60 |
| gccaggatcc ctgaattctc aggttggttg ctagaggtcc ccaatgggcc ctggaggtcc | 120 |
| ctcaccttct acccagcctg gctcacagtg tcagagggag caaatgccac cttcacctgc | 180 |
| agcttgtcca actggtcgga ggatcttatg ctgaactgga accgcctgag tcccagcaac | 240 |
| cagactgaaa acaggccgc cttcgtaat ggtttgagcc aacccgtcca ggatgcccgc | 300 |
| ttccagatca tacagctgcc caacaggcat gacttccaca tgaacatcct tgacacacgg | 360 |
| cgcaatgaca gtggcatcta cctctgtggg gccatctccc tgcaccccaa ggcaaaaatc | 420 |
| gaggagagcc ctggagcaga gctcgtggta acagagagaa tcctggagac ctcaacaaga | 480 |
| tatcccagcc cctcgcccaa accagaaggc cggtttcaag catggttca attcaccact | 540 |
| gatgctgccc atcctggaag gtctgtggtg cctgccttgc tgcctctgct ggctggcact | 600 |
| ctgctgctgc tggagactgc cactgctccc taa | 633 |

<210> SEQ ID NO 12
<211> LENGTH: 531
<212> TYPE: DNA
<213> ORGANISM: Artificial Sequence
<220> FEATURE:
<223> OTHER INFORMATION: IL2ss-mPD-1

<400> SEQUENCE: 12

| | |
|---|---|
| atgtatagga tgcaactgct gtcttgcatt gctctgtctc tggcactggt cactaactct | 60 |
| gccaggatcc ctgaattctc aggttggttg ctagaggtcc ccaatgggcc ctggaggtcc | 120 |
| ctcaccttct acccagcctg gctcacagtg tcagagggag caaatgccac cttcacctgc | 180 |
| agcttgtcca actggtcgga ggatcttatg ctgaactgga accgcctgag tcccagcaac | 240 |
| cagactgaaa acaggccgc cttcgtaat ggtttgagcc aacccgtcca ggatgcccgc | 300 |
| ttccagatca tacagctgcc caacaggcat gacttccaca tgaacatcct tgacacacgg | 360 |
| cgcaatgaca gtggcatcta cctctgtggg gccatctccc tgcaccccaa ggcaaaaatc | 420 |
| gaggagagcc ctggagcaga gctcgtggta acagagagaa tcctggagac ctcaacaaga | 480 |
| tatcccagcc cctcgcccaa accagaaggc cggtttcaag catggttta a | 531 |

<210> SEQ ID NO 13
<211> LENGTH: 513
<212> TYPE: DNA
<213> ORGANISM: Artificial Sequence
<220> FEATURE:
<223> OTHER INFORMATION: IL2ss-mPD-L1-PLAP

<400> SEQUENCE: 13

| | |
|---|---|
| atgtatagga tgcaactgct gtcttgcatt gctctgtctc tggcactggt cactaactct | 60 |
| gccaggatcc ctgaattcat gtttactatc acggctccaa aggacttgta cgtggtggag | 120 |

```
tatggcagca acgtcacgat ggagtgcaga ttccctgtag aacgggagct ggacctgctt      180
gcgttagtgg tgtactggga aaaggaagat gagcaagtga ttcagtttgt ggcaggagag      240
gaggacctta agcctcagca cagcaacttc agggggagag cctcgctgcc aaaggaccag      300
cttttgaagg gaaatgctgc ccttcagatc acagacgtca agctgcagga cgcaggcgtt      360
tactgctgca taatcagcta cggtggtgcg gactacaagc gaatcacgca attcaccact      420
gatgctgccc atcctggaag gtctgtggtg cctgccttgc tgcctctgct ggctggcact      480
ctgctgctgc tggagactgc cactgctccc taa                                  513

<210> SEQ ID NO 14
<211> LENGTH: 411
<212> TYPE: DNA
<213> ORGANISM: Artificial Sequence
<220> FEATURE:
<223> OTHER INFORMATION: IL2ss-mPD-L1

<400> SEQUENCE: 14
atgtatagga tgcaactgct gtcttgcatt gctctgtctc tggcactggt cactaactct       60
gccaggatcc ctgaattcat gtttactatc acggctccaa aggacttgta cgtggtggag      120
tatggcagca acgtcacgat ggagtgcaga ttccctgtag aacgggagct ggacctgctt      180
gcgttagtgg tgtactggga aaaggaagat gagcaagtga ttcagtttgt ggcaggagag      240
gaggacctta agcctcagca cagcaacttc agggggagag cctcgctgcc aaaggaccag      300
cttttgaagg gaaatgctgc ccttcagatc acagacgtca agctgcagga cgcaggcgtt      360
tactgctgca taatcagcta cggtggtgcg gactacaagc gaatcacgta a               411

<210> SEQ ID NO 15
<211> LENGTH: 1020
<212> TYPE: DNA
<213> ORGANISM: Artificial Sequence
<220> FEATURE:
<223> OTHER INFORMATION: IL2ss-mCTLA4-mPD-1-PLAP

<400> SEQUENCE: 15
atgtatagga tgcaactgct gtcttgcatt gctctgtctc tggcactggt cactaactct       60
gccaggatcc ctgaattcat ggaagccata caggtgaccc aaccttcagt ggtgttggct      120
agcagccatg tgtcgccag cttttccatgt gaatattcac cgtcacacaa cactgatgag      180
gtccgggtga ctgtgctgcg gcagacaaat gaccaaatga ctgaggtctg tgccacgaca      240
ttcacagaga agaatacagt gggcttccta gattacccct tctgcagtgg taccttta at      300 gaaagcagag tgaacctcac catccaagga ctgagagctg ttgacacggg actgtacctc      360
tgcaaggtgg aactcatgta cccaccgcca tactttgtgg gcatgggcaa cgggacgcag      420
atttatgtca ttgatccaga accatgcccg gattctgacc aattctcagg ttggttgcta      480
gaggtcccca tgggccctg aggtccctc accttctacc cagcctggct cacagtgtca      540
gagggagcaa atgccacctt cacctgcagc ttgtccaact ggtcgaggga tcttatgctg      600
aactggaacc gcctgagtcc cagcaaccag actgaaaaac aggccgcctt ctgtaatggt      660
ttgagccaac ccgtccagga tgcccgcttc cagatcatac agctgcccaa caggcatgac      720
ttccacatga acatccttga cacacggcgc aatgacagtg gcatctacct ctgtgggcc      780 atctcctgc accccaaggc aaaaatcgag gagagccctg gagcagagct cgtggtaaca      840
gagagaatcc tggagacctc aacaagatat cccagcccct cgcccaaacc agaaggccgg      900
tttcaaggca tggttcaatt caccactgat gctgcccatc ctggaaggtc tgtggtgcct      960
```

```
gccttgctgc tctgctggc tggcactctg ctgctgctgg agactgccac tgctccctaa    1020
```

<210> SEQ ID NO 16
<211> LENGTH: 918
<212> TYPE: DNA
<213> ORGANISM: Artificial Sequence
<220> FEATURE:
<223> OTHER INFORMATION: IL2ss-mCTLA4-mPD-1

<400> SEQUENCE: 16

```
atgtatagga tgcaactgct gtcttgcatt gctctgtctc tggcactggt cactaactct     60
gccaggatcc ctgaattcat ggaagccata caggtgaccc aaccttcagt ggtgttggct    120
agcagccatg gtgtcgccag ctttccatgt gaatattcac cgtcacacaa cactgatgag    180
gtccgggtga ctgtgctgcg gcagacaaat gaccaaatga ctgaggtctg tgccacgaca    240
ttcacagaga agaatacagt gggcttccta gattacccct tctgcagtgg tacctttaat    300
gaaagcagag tgaacctcac catccaagga ctgagagctg ttgacacggg actgtacctc    360
tgcaaggtgg aactcatgta cccaccgcca tactttgtgg gcatgggcaa cgggacgcag    420
atttatgtca ttgatccaga accatgcccg gattctgacc aattctcagg ttggttgcta    480
gaggtcccca atgggccctg gaggtccctc accttctacc cagcctggct cacagtgtca    540
gagggagcaa atgccacctt cacctgcagc ttgtccaact ggtcggagga tcttatgctg    600
aactggaacc gcctgagtcc cagcaaccag actgaaaaac aggccgcctt ctgtaatggt    660
ttgagccaac ccgtccagga tgcccgcttc cagatcatac agctgcccaa caggcatgac    720
ttccacatga acatccttga cacacggcgc aatgacagtg catctacct ctgtgggcc     780
atctccctgc accccaaggc aaaaatcgag gagagccctg gagcagagct cgtggtaaca    840
gagagaatcc tggagacctc aacaagatat cccagccccc gcccaaacc agaaggccgg     900
tttcaaggca tggtttaa                                                 918
```

<210> SEQ ID NO 17
<211> LENGTH: 900
<212> TYPE: DNA
<213> ORGANISM: Artificial Sequence
<220> FEATURE:
<223> OTHER INFORMATION: IL2ss-mCTLA4-mPD-L1-PLAP

<400> SEQUENCE: 17

```
atgtatagga tgcaactgct gtcttgcatt gctctgtctc tggcactggt cactaactct     60
gccaggatcc ctgaattcat ggaagccata caggtgaccc aaccttcagt ggtgttggct    120
agcagccatg gtgtcgccag ctttccatgt gaatattcac cgtcacacaa cactgatgag    180
gtccgggtga ctgtgctgcg gcagacaaat gaccaaatga ctgaggtctg tgccacgaca    240
ttcacagaga agaatacagt gggcttccta gattacccct tctgcagtgg tacctttaat    300
gaaagcagag tgaacctcac catccaagga ctgagagctg ttgacacggg actgtacctc    360
tgcaaggtgg aactcatgta cccaccgcca tactttgtgg gcatgggcaa cgggacgcag    420
atttatgtca ttgatccaga accatgcccg gattctgacc aattcatgtt tactatcacg    480
gctccaaagg acttgtacgt ggtggagtat ggcagcaacg tcacgatgga gtgcagattc    540
cctgtagaac gggagctgga cctgcttgcg ttagtggtgt actgggaaaa ggaagatgag    600
caagtgattc agtttgtggc aggagaggag gaccttaagc tcagcacag caacttcagg    660
gggagagcct cgctgccaaa ggaccagctt ttgaagggaa atgctgccct tcagatcaca    720
```

| | | |
|---|---|---|
| gacgtcaagc tgcaggacgc aggcgtttac tgctgcataa tcagctacgg tggtgcggac | 780 | |
| tacaagcgaa tcacgcaatt caccactgat gctgcccatc ctggaaggtc tgtggtgcct | 840 | |
| gccttgctgc ctctgctggc tggcactctg ctgctgctgg agactgccac tgctccctaa | 900 | |

<210> SEQ ID NO 18
<211> LENGTH: 798
<212> TYPE: DNA
<213> ORGANISM: Artificial Sequence
<220> FEATURE:
<223> OTHER INFORMATION: IL2ss-mCTLA4-mPD-L1

<400> SEQUENCE: 18

| | | |
|---|---|---|
| atgtataggatgcaactgct gtcttgcatt gctctgtctc tggcactggt cactaactct | 60 | |
| gccaggatcc ctgaattcat ggaagccata caggtgaccc aaccttcagt ggtgttggct | 120 | |
| agcagccatg gtgtcgccag ctttccatgt gaatattcac cgtcacacaa cactgatgag | 180 | |
| gtccgggtga ctgtgctgcg gcagacaaat gaccaaatga ctgaggtctg tgccacgaca | 240 | |
| ttcacagaga agaatacagt gggcttccta gattacccct ctgcagtgg taccttaat | 300 | |
| gaaagcagag tgaacctcac catccaagga ctgagagctg ttgacacggg actgtacctc | 360 | |
| tgcaaggtgg aactcatgta cccaccgcca tactttgtgg gcatgggcaa cgggacgcag | 420 | |
| atttatgtca ttgatccaga accatgcccg gattctgacc aattcatgtt tactatcacg | 480 | |
| gctccaaagg acttgtacgt ggtggagtat ggcagcaacg tcacgatgga gtgcagattc | 540 | |
| cctgtagaac gggagctgga cctgcttgcg ttagtggtgt actgggaaaa ggaagatgag | 600 | |
| caagtgattc agtttgtggc aggagaggag gaccttaagc ctcagcacag caacttcagg | 660 | |
| gggagagcct cgctgccaaa ggaccagctt ttgaagggaa atgctgccct tcagatcaca | 720 | |
| gacgtcaagc tgcaggacgc aggcgtttac tgctgcataa tcagctacgg tggtgcggac | 780 | |
| tacaagcgaa tcacgtaa | 798 | |

<210> SEQ ID NO 19
<211> LENGTH: 63
<212> TYPE: DNA
<213> ORGANISM: Homo sapiens

<400> SEQUENCE: 19

| | | |
|---|---|---|
| atgtataggatgcaactgct gtcttgcatt gctctgtctc tggcactggt cactaactct | 60 | |
| gcc | 63 | |

<210> SEQ ID NO 20
<211> LENGTH: 96
<212> TYPE: DNA
<213> ORGANISM: Homo sapiens

<400> SEQUENCE: 20

| | | |
|---|---|---|
| accactgatg ctgcccatcc tggaaggtct gtggtgcctg ccttgctgcc tctgctggct | 60 | |
| ggcactctgc tgctgctgga gactgccact gctccc | 96 | |

<210> SEQ ID NO 21
<211> LENGTH: 372
<212> TYPE: DNA
<213> ORGANISM: Homo sapiens

<400> SEQUENCE: 21

| | | |
|---|---|---|
| gcaatgcacg tggcccagcc tgctgtggta ctggccagca gccgaggcat cgccagcttt | 60 | |
| gtgtgtgagt atgcatctcc aggcaaagcc actgaggtcc gggtgacagt gcttcggcag | 120 | |

```
gctgacagcc aggtgactga agtctgtgcg gcaacctaca tgatggggaa tgagttgacc    180
ttcctagatg attccatctg cacgggcacc tccagtggaa atcaagtgaa cctcactatc    240
caaggactga gggccatgga cacgggactc tacatctgca aggtggagct catgtaccca    300
ccgccatact acctgggcat aggcaacgga acccagattt atgtaattga tccagaaccg    360
tgcccagatt ct                                                         372

<210> SEQ ID NO 22
<211> LENGTH: 378
<212> TYPE: DNA
<213> ORGANISM: Mus musculus

<400> SEQUENCE: 22
gaagccatac aggtgaccca accttcagtg gtgttggcta gcagccatgg tgtcgccagc     60
tttccatgtg aatattcacc gtcacacaac actgatgagg tccgggtgac tgtgctgcgg    120
cagacaaatg accaaatgac tgaggtctgt gccacgacat tcacagagaa gaatacagtg    180
ggcttcctag attaccccctt ctgcagtggt acctttaatg aaagcagagt gaacctcacc    240
atccaaggac tgagagctgt tgacacggga ctgtacctct gcaaggtgga actcatgtac    300
ccaccgccat actttgtggg catgggcaac gggacgcaga tttatgtcat tgatccagaa    360
ccatgcccgg attctgac                                                   378

<210> SEQ ID NO 23
<211> LENGTH: 450
<212> TYPE: DNA
<213> ORGANISM: Homo sapiens

<400> SEQUENCE: 23
ccaggatggt tcttagactc cccagacagg ccctggaacc cccccacctt ctccccagcc     60
ctgctcgtgg tgaccgaagg ggacaacgcc accttcacct gcagcttctc caacacatcg    120
gagagcttcg tgctaaactg gtaccgcatg agccccagca ccagacggga caagctggcc    180
gccttccccg aggaccgcag ccagcccggc caggactgcc gcttccgtgt cacacaactg    240
cccaacgggc gtgacttcca catgagcgtg gtcagggccg gcgcaatgac agcggcacc    300 tacctctgtg gggccatctc cctggccccc aaggcgcaga tcaaagagag cctgcgggca    360
gagctcaggg tgacagagag aagggcagaa gtgcccacag cccaccccag cccctcaccc    420
aggccagccg gccagttcca aaccctggtg                                      450

<210> SEQ ID NO 24
<211> LENGTH: 450
<212> TYPE: DNA
<213> ORGANISM: Mus musculus

<400> SEQUENCE: 24
tcaggttggt tgctagaggt ccccaatggg ccctggaggt ccctcacctt ctacccagcc     60
tggctcacag tgtcagaggg agcaaatgcc accttcacct gcagcttgtc caactggtcg    120
gaggatctta tgctgaactg gaaccgcctg agtcccagca accagactga aaaacaggcc    180
gccttctgta atggtttgag ccaacccgtc caggatgccc gcttccagat catacagctg    240
cccaacaggc atgacttcca catgaacatc cttgacacac ggcgcaatga cagtggcatc    300
tacctctgtg gggccatctc cctgcacccc aaggcaaaaa tcgaggagag ccctggagca    360
gagctcgtgg taacagagag aatcctggag acctcaacaa gatatcccag cccctcgccc    420
```

```
aaaccagaag gccggtttca aggcatggtt                                     450
```

<210> SEQ ID NO 25
<211> LENGTH: 660
<212> TYPE: DNA
<213> ORGANISM: Homo sapiens

<400> SEQUENCE: 25

```
ttcactgtca cggttcccaa ggacctatat gtggtagagt atggtagcaa tatgacaatt     60
gaatgcaaat tcccagtaga aaacaatta gacctggctg cactaattgt ctattgggaa     120
atggaggata gaacattat tcaatttgtg catggagagg aagacctgaa ggttcagcat     180
agtagctaca gacagagggc ccggctgttg aaggaccagc tctccctggg aaatgctgca    240
cttcagatca cagatgtgaa attgcaggat gcagggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga dattttctac tgcactttta ggagattaga tcctgaggaa    600
aaccatacag ctgaattggt catcccagaa ctacctctgg cacatcctcc aaatgaaagg    660
```

<210> SEQ ID NO 26
<211> LENGTH: 327
<212> TYPE: DNA
<213> ORGANISM: Mus musculus

<400> SEQUENCE: 26

```
tttactatca cggctccaaa ggacttgtac gtggtggagt atggcagcaa cgtcacgatg     60
gagtgcagat tccctgtaga acgggagctg gacctgcttg cgttagtggt gtactgggaa    120
aaggaagatg agcaagtgat tcagtttgtg gcaggagagg aggaccttaa gcctcagcac    180
agcaacttca gggggagagc ctcgctgcca aaggaccagc ttttgaaggg aaatgctgcc    240
cttcagatca cagacgtcaa gctgcaggac gcaggcgttt actgctgcat aatcagctac    300
ggtggtgcgg actacaagcg aatcacg                                        327
```

<210> SEQ ID NO 27
<211> LENGTH: 828
<212> TYPE: DNA
<213> ORGANISM: Artificial Sequence
<220> FEATURE:
<223> OTHER INFORMATION: hCTLA4-hPD-1

<400> SEQUENCE: 27

```
gcaatgcacg tggcccagcc tgctgtggta ctggccagca gccgaggcat cgccagcttt     60
gtgtgtgagt atgcatctcc aggcaaagcc actgaggtcc gggtgacagt gcttcggcag    120
gctgacagcc aggtgactga agtctgtgcg gcaacctaca tgatggggaa tgagttgacc    180
ttcctagatg attccatctg cacgggcacc tccagtggaa atcaagtgaa cctcactatc    240
caaggactga gggccatgga cacgggactc tacatctgca aggtggagct catgtaccca    300
ccgccatact acctgggcat aggcaacgga acccagattt atgtaattga tccagaaccg    360
tgcccagatt ctgaattccc aggatggttc ttagactccc agacaggcc ctggaacccc    420 cccaccttct cccagccct gctcgtggtg accgaagggg acaacgccac cttcacctgc    480
agcttctcca acacatcgga gagcttcgtg ctaaactggt accgcatgag ccccagcaac    540
```

```
cagacggaca agctggccgc cttccccgag gaccgcagcc agcccggcca ggactgccgc      600
ttccgtgtca cacaactgcc caacgggcgt gacttccaca tgagcgtggt cagggcccgg      660
cgcaatgaca gcggcaccta cctctgtggg gccatctccc tggcccccaa ggcgcagatc      720
aaagagagcc tgcgggcaga gctcagggtg acagagagaa gggcagaagt gcccacagcc      780
caccccagcc cctcacccag gccagccggc cagttccaaa ccctggtg                   828
```

```
<210> SEQ ID NO 28
<211> LENGTH: 1035
<212> TYPE: DNA
<213> ORGANISM: Artificial Sequence
<220> FEATURE:
<223> OTHER INFORMATION: hCTLA4-hPD-L1

<400> SEQUENCE: 28
```

```
gcaatgcacg tggcccagcc tgctgtggta ctggccagca gccgaggcat cgccagcttt      60
gtgtgtgagt atgcatctcc aggcaaagcc actgaggtcc gggtgacagt gcttcggcag     120
gctgacagcc aggtgactga agtctgtgcg gcaacctaca tgatggggaa tgagttgacc     180
ttcctagatg attccatctg cacgggcacc tccagtggaa atcaagtgaa cctcactatc     240
caaggactga gggccatgga cacgggactc tacatctgca aggtggagct catgtaccca     300
ccgccatact acctgggcat aggcaacgga acccagattt atgtaattga tccagaaccg     360
tgcccagatt ctgaattcac tgtcacggtt cccaaggacc tatatgtggt agagtatggt     420
agcaatatga caattgaatg caaattccca gtagaaaaac aattagacct ggctgcacta     480
attgtctatt gggaaatgga ggataagaac attattcaat ttgtgcatgg agaggaagac     540
ctgaaggttc agcatagtag ctacagacag agggcccggc tgttgaagga ccagctctcc     600
ctgggaaatg ctgcacttca gatcacagat gtgaaattgc aggatgcagg ggtgtaccgc     660
tgcatgatca gctatggtgg tgccgactac aagcgaatta ctgtgaaagt caatgcccca     720
tacaacaaaa tcaaccaaag aattttggtt gtggatccag tcacctctga acatgaactg     780
acatgtcagg ctgagggcta ccccaaggcc gaagtcatct ggacaagcag tgaccatcaa     840
gtcctgagtg gtaagaccac caccaccaat tccaagagag aggagaagct ttcaatgtg      900 accagcacac tgagaataaa cacaacaact aatgagattt ctactgcac ttttaggaga     960 ttagatcctg aggaaaacca tacagctgaa ttggtcatcc cagaactacc tctggcacat    1020
cctccaaatg aaagg                                                     1035
```

```
<210> SEQ ID NO 29
<211> LENGTH: 834
<212> TYPE: DNA
<213> ORGANISM: Artificial Sequence
<220> FEATURE:
<223> OTHER INFORMATION: mCTLA4-mPD-1

<400> SEQUENCE: 29
```

```
gaagccatac aggtgaccca accttcagtg gtgttggcta gcagccatgg tgtcgccagc      60
tttccatgtg aatattcacc gtcacacaac actgatgagg tccgggtgac tgtgctgcgg     120
cagacaaatg accaaatgac tgaggtctgt gccacgacat tcacagagaa gaatacagtg     180
ggcttcctag attaccccctt ctgcagtggt acctttaatg aaagcagagt gaacctcacc     240
atccaaggac tgagagctgt tgacacggga ctgtacctct gcaaggtgga actcatgtac     300
ccaccgccat actttgtggg catgggcaac ggaacgcaga tttatgtcat tgatccagaa     360
```

```
ccatgcccgg attctgacca attctcaggt tggttgctag aggtccccaa tgggccctgg      420
aggtccctca ccttctaccc agcctggctc acagtgtcag agggagcaaa tgccaccttc      480
acctgcagct tgtccaactg gtcggaggat cttatgctga actggaaccg cctgagtccc      540
agcaaccaga ctgaaaaaca ggccgccttc tgtaatggtt tgagccaacc cgtccaggat      600
gcccgcttcc agatcataca gctgcccaac aggcatgact tccacatgaa catccttgac      660
acacggcgca atgacagtgg catctacctc tgtggggcca tctccctgca ccccaaggca      720
aaaatcgagg agagccctgg agcagagctc gtggtaacag agagaatcct ggagacctca      780
acaagatatc ccagcccctc gcccaaacca gaaggccggt tcaaggcat ggtt            834
```

```
<210> SEQ ID NO 30
<211> LENGTH: 714
<212> TYPE: DNA
<213> ORGANISM: Artificial Sequence
<220> FEATURE:
<223> OTHER INFORMATION: mCTLA4-mPD-L1

<400> SEQUENCE: 30
gaagccatac aggtgaccca accttcagtg gtgttggcta gcagccatgg tgtcgccagc      60
tttccatgtg aatattcacc gtcacacaac actgatgagg tccgggtgac tgtgctgcgg     120
cagacaaatg accaaatgac tgaggtctgt gccacgacat tcacagagaa gaatacagtg     180
ggcttcctag attacccctt ctgcagtggt acctttaatg aaagcagagt gaacctcacc     240
atccaaggac tgagagctgt tgacacggga ctgtacctct gcaaggtgga actcatgtac     300
ccaccgccat actttgtggg catgggcaac gggacgcaga tttatgtcat tgatccagaa     360
ccatgcccgg attctgacca attcatgttt actatcacgg ctccaaagga cttgtacgtg     420
gtggagtatg gcagcaacgt cacgatggag tgcagattcc tgtagaacg ggagctggac     480 ctgcttgcgt tagtggtgta ctgggaaaag gaagatgagc aagtgattca gtttgtggca     540
ggagaggagg accttaagcc tcagcacagc aacttcaggg ggagagcctc gctgccaaag     600
gaccagcttt tgaagggaaa tgctgcccct cagatcacag acgtcaagct gcaggacgca     660
ggcgtttact gctgcataat cagctacggt ggtgcggact acaagcgaat cacg           714
```

```
<210> SEQ ID NO 31
<211> LENGTH: 288
<212> TYPE: PRT
<213> ORGANISM: Artificial Sequence
<220> FEATURE:
<223> OTHER INFORMATION: mCTLA4-mPD1-6His

<400> SEQUENCE: 31

Met Met Glu Ala Ile Gln Val Thr Gln Pro Ser Val Val Leu Ala Ser
1               5                   10                  15

Ser His Gly Val Ala Ser Phe Pro Cys Glu Tyr Ser Pro Ser His Asn
                20                  25                  30

Thr Asp Glu Val Arg Val Thr Val Leu Arg Gln Thr Asn Asp Gln Met
        35                  40                  45

Thr Glu Val Cys Ala Thr Thr Phe Thr Glu Lys Asn Thr Val Gly Phe
    50                  55                  60

Leu Asp Tyr Pro Phe Cys Ser Gly Thr Phe Asn Glu Ser Arg Val Asn
65                  70                  75                  80

Leu Thr Ile Gln Gly Leu Arg Ala Val Asp Thr Gly Leu Tyr Leu Cys
                85                  90                  95

Lys Val Glu Leu Met Tyr Pro Pro Pro Tyr Phe Val Gly Met Gly Asn
```

```
            100                 105                 110
Gly Thr Gln Ile Tyr Val Ile Asp Pro Glu Pro Cys Pro Asp Ser Asp
            115                 120                 125

Gln Phe Ser Gly Trp Leu Leu Glu Val Pro Asn Gly Pro Trp Arg Ser
        130                 135                 140

Leu Thr Phe Tyr Pro Ala Trp Leu Thr Val Ser Glu Gly Ala Asn Ala
145                 150                 155                 160

Thr Phe Thr Cys Ser Leu Ser Asn Trp Ser Glu Asp Leu Met Leu Asn
                165                 170                 175

Trp Asn Arg Leu Ser Pro Ser Asn Gln Thr Glu Lys Gln Ala Ala Phe
            180                 185                 190

Cys Asn Gly Leu Ser Gln Pro Val Gln Asp Ala Arg Phe Gln Ile Ile
        195                 200                 205

Gln Leu Pro Asn Arg His Asp Phe His Met Asn Ile Leu Asp Thr Arg
    210                 215                 220

Arg Asn Asp Ser Gly Ile Tyr Leu Cys Gly Ala Ile Ser Leu His Pro
225                 230                 235                 240

Lys Ala Lys Ile Glu Glu Ser Pro Gly Ala Glu Leu Val Val Thr Glu
                245                 250                 255

Arg Ile Leu Glu Thr Ser Thr Arg Tyr Pro Ser Pro Ser Pro Lys Pro
            260                 265                 270

Glu Gly Arg Phe Gln Gly Met Val Leu Glu His His His His His His
        275                 280                 285

<210> SEQ ID NO 32
<211> LENGTH: 248
<212> TYPE: PRT
<213> ORGANISM: Artificial Sequence
<220> FEATURE:
<223> OTHER INFORMATION: mCTLA4-mPDL1-6His

<400> SEQUENCE: 32

Met Met Glu Ala Ile Gln Val Thr Gln Pro Ser Val Val Leu Ala Ser
1               5                   10                  15

Ser His Gly Val Ala Ser Phe Pro Cys Glu Tyr Ser Pro Ser His Asn
            20                  25                  30

Thr Asp Glu Val Arg Val Thr Val Leu Arg Gln Thr Asn Asp Gln Met
        35                  40                  45

Thr Glu Val Cys Ala Thr Thr Phe Thr Glu Lys Asn Thr Val Gly Phe
    50                  55                  60

Leu Asp Tyr Pro Phe Cys Ser Gly Thr Phe Asn Glu Ser Arg Val Asn
65                  70                  75                  80

Leu Thr Ile Gln Gly Leu Arg Ala Val Asp Thr Gly Leu Tyr Leu Cys
                85                  90                  95

Lys Val Glu Leu Met Tyr Pro Pro Tyr Phe Val Gly Met Gly Asn
            100                 105                 110

Gly Thr Gln Ile Tyr Val Ile Asp Pro Glu Pro Cys Pro Asp Ser Asp
        115                 120                 125

Gln Phe Met Phe Thr Ile Thr Ala Pro Lys Asp Leu Tyr Val Val Glu
    130                 135                 140

Tyr Gly Ser Asn Val Thr Met Glu Cys Arg Phe Pro Val Glu Arg Glu
145                 150                 155                 160

Leu Asp Leu Leu Ala Leu Val Val Tyr Trp Glu Lys Glu Asp Glu Gln
                165                 170                 175

Val Ile Gln Phe Val Ala Gly Glu Glu Asp Leu Lys Pro Gln His Ser
```

```
              180                 185                 190
Asn Phe Arg Gly Arg Ala Ser Leu Pro Lys Asp Gln Leu Leu Lys Gly
            195                 200                 205

Asn Ala Ala Leu Gln Ile Thr Asp Val Lys Leu Gln Asp Ala Gly Val
        210                 215                 220

Tyr Cys Cys Ile Ile Ser Tyr Gly Gly Ala Asp Tyr Lys Arg Ile Thr
225                 230                 235                 240

Leu Glu His His His His His His
                245

<210> SEQ ID NO 33
<211> LENGTH: 1131
<212> TYPE: DNA
<213> ORGANISM: Artificial Sequence
<220> FEATURE:
<223> OTHER INFORMATION: pVAC1-IL2ss-hCTLA4-hPD1(31-147aa)-
      hPDL1(19-127aa)

<400> SEQUENCE: 33
```
atgtataggu tgcaactgct gtcttgcatt gctctgtctc tggcactggt cactaactct      60
gccaggatcc tggcaatgca cgtggcccag cctgctgtgg tactggccag cagccgaggc     120
atcgccagct tgtgtgtga gtatgcatct ccaggcaaag ccactgaggt ccgggtgaca      180
gtgcttcggc aggctgacag ccaggtgact gaagtctgtg cggcaaccta catgatgggg     240
aatgagttga ccttcctaga tgattccatc tgcacgggca cctccagtgg aaatcaagtg     300
aacctcacta tccaaggact gagggccatg gacacgggac tctacatctg caaggtggag     360
ctcatgtacc caccgccata ctacctgggc ataggcaacg gaacccagat ttatgtaatt     420
gatccagaac cgtgcccaga ttctgaattg ccctggaacc cccccaccttt ctccccagcc    480 ctgctcgtgg tgaccgaagg ggacaacgcc accttcacct gcagcttctc caacacatcg     540
gagagcttcg tgctaaactg gtaccgcatg agccccagca accagacgga caagctggcc     600
gccttccccg aggaccgcag ccagcccggc caggactgcc gcttccgtgt cacacaactg     660
cccaacgggc gtgacttcca catgagcgtg gtcagggccc ggcgcaatga cagcggcacc     720
tacctctgtg gggccatctc cctggccccc aaggcgcaga tcaaagagag cctgcgggca     780
gagctcaggg tgacagagag agaattcact gtcacggttc ccaaggacct atatgtggta     840
gagtatggta gcaatatgac aattgaatgc aaattcccag tagaaaaaca attagacctg     900
gctgcactaa ttgtctattg ggaaatggag ataagaaaca ttattcaatt tgtgcatgga     960
gaggaagacc tgaaggttca gcatagtagc tacagacaga gggcccggct gttgaaggac    1020
cagctctccc tgggaaatgc tgcacttcag atcacagatg tgaaattgca ggatgcaggg    1080
gtgtaccgct gcatgatcag ctatggtggt gccgactaca agcgaattac t             1131

```
<210> SEQ ID NO 34
<211> LENGTH: 1464
<212> TYPE: DNA
<213> ORGANISM: Artificial Sequence
<220> FEATURE:
<223> OTHER INFORMATION: pVAC1-IL2ss-hCTLA4-hPD1(31-147aa)-
      hPDL1(19-238aa)

<400> SEQUENCE: 34
```
atgtataggu tgcaactgct gtcttgcatt gctctgtctc tggcactggt cactaactct      60
gccaggatcc tggcaatgca cgtggcccag cctgctgtgg tactggccag cagccgaggc     120
atcgccagct tgtgtgtga gtatgcatct ccaggcaaag ccactgaggt ccgggtgaca      180

```
gtgcttcggc aggctgacag ccaggtgact gaagtctgtg cggcaaccta catgatgggg    240
aatgagttga ccttcctaga tgattccatc tgcacgggca cctccagtgg aaatcaagtg    300
aacctcacta tccaaggact gagggccatg gacacgggac tctacatctg caaggtggag    360
ctcatgtacc caccgccata ctacctgggc ataggcaacg gaacccagat ttatgtaatt    420
gatccagaac cgtgcccaga ttctgaattg ccctggaacc ccccaccttt ctccccagcc    480
ctgctcgtgg tgaccgaagg ggacaacgcc accttcacct gcagcttctc caacacatcg    540
gagagcttcg tgctaaactg gtaccgcatg agcccagca accagacgga caagctggcc     600
gccttccccg aggaccgcag ccagcccggc caggactgcc gcttccgtgt cacacaactg    660
cccaacgggc gtgacttcca catgagcgtg gtcagggccc ggcgcaatga cagcggcacc    720
tacctctgtg gggccatctc cctggccccc aaggcgcaga tcaaagagag cctgcgggca    780
gagctcaggg tgacagagag agaattcact gtcacggttc caaggacct atatgtggta     840 gagtatggta gcaatatgac aattgaatgc aaattcccag tagaaaaaca attagacctg    900
gctgcactaa ttgtctattg ggaaatggag gataagaaca ttattcaatt tgtgcatgga    960
gaggaagacc tgaaggttca gcatagtagc tacagacaga gggcccggct gttgaaggac   1020
cagctctccc tgggaaatgc tgcacttcag atcacagatg tgaaattgca ggatgcaggg   1080
gtgtaccgct gcatgatcag ctatggtggt gccgactaca gcgaattac tgtgaaagtc    1140 aatgccccat acaacaaaat caaccaaaga attttggttg tggatccagt cacctctgaa   1200
catgaactga catgtcaggc tgagggctac cccaaggccg aagtcatctg gacaagcagt   1260
gaccatcaag tcctgagtgg taagaccacc accaccaatt ccaagagaga ggagaagctt   1320
ttcaatgtga ccagcacact gagaatcaac acaacaacta atgagatttt ctactgcact   1380
tttaggagat tagatcctga ggaaaaccat acagctgaat ggtcatccc agaactacct    1440 ctggcacatc ctccaaatga aagg                                          1464
```

<210> SEQ ID NO 35
<211> LENGTH: 1143
<212> TYPE: DNA
<213> ORGANISM: Artificial Sequence
<220> FEATURE:
<223> OTHER INFORMATION: pVAC1-IL2ss-mCTLA4-mPD1(31-147aa)-
      mPDL1(19-127aa)

<400> SEQUENCE: 35

```
atgtatagga tgcaactgct gtcttgcatt gctctgtctc tggcactggt cactaactct     60
gccaggatcc ctgaattcat ggaagccata caggtgaccc aaccttcagt ggtgttggct    120
agcagccatg gtgtcgccag ctttccatgt gaatattcac cgtcacacaa cactgatgag    180
gtccgggtga ctgtgctgcg gcagacaaat gaccaaatga ctgaggtctg tgccacgaca    240
ttcacagaga agaatacagt gggcttccta gattacccct ctgcagtgg tacctttaat    300 gaaagcagag tgaacctcac catccaagga ctgagagctt tgacacggg actgtacctc    360 tgcaaggtgg aactcatgta cccaccgcca tactttgtgg gcatgggcaa cgggacgcag    420
atttatgtca ttgatccaga accatgcccg gattctgata tccccctggag gtccctcacc    480 ttctacccag cctggctcac agtgtcagag ggagcaaatg ccacttcac ctgcagcttg    540 tccaactggt cggaggatct tatgctgaac tggaaccgcc tgagtccag caaccagact    600 gaaaaacagg ccgccttctg taatggtttg agccaacccg tccaggatgc cgcttccag    660 atcatacagc tgcccaacag gcatgacttc cacatgaaca tccttgacac acggcgcaat    720
```

```
gacagtggca tctacctctg tggggccatc tccctgcacc ccaaggcaaa aatcgaggag    780
agccctggag cagagctcgt ggtaacagag agatctttta ctatcacggc tccaaaggac    840
ttgtacgtgg tggagtatgg cagcaacgtc acgatggagt gcagattccc tgtagaacgg    900
gagctggacc tgcttgcgtt agtggtgtac tgggaaaagg aagatgagca agtgattcag    960
tttgtggcag gagaggagga ccttaagcct cagcacagca acttcagggg gagagcctcg   1020
ctgccaaagg accagctttt gaagggaaat gctgcccttc agatcacaga cgtcaagctg   1080
caggacgcag gcgtttactg ctgcataatc agctacggtg gtgcggacta caagcgaatc   1140
acg                                                                 1143

<210> SEQ ID NO 36
<211> LENGTH: 1473
<212> TYPE: DNA
<213> ORGANISM: Artificial Sequence
<220> FEATURE:
<223> OTHER INFORMATION: pVAC1-IL2ss-mCTLA4-mPD1(31-147aa)-
      mPDL1(19-237aa)

<400> SEQUENCE: 36
atgtatagga tgcaactgct gtcttgcatt gctctgtctc tggcactggt cactaactct     60
gccaggatcc ctgaattcat ggaagccata caggtgaccc aaccttcagt ggtgttggct    120
agcagccatg tgtcgccag ctttccatgt gaatattcac cgtcacacaa cactgatgag    180
gtccgggtga ctgtgctgcg cagacaaat gaccaaatga ctgaggtctg tgccacgaca    240
ttcacagaga agaatacagt gggcttccta gattacccct tctgcagtgg tacctttaat    300
gaaagcagag tgaacctcac catccaagga ctgagagctg ttgacacggg actgtacctc    360 tgcaaggtg aactcatgta cccaccgcca tactttgtgg gcatgggcaa cgggacgcag    420
atttatgtca ttgatccaga accatgcccg gattctgata tccctggag gtccctcacc    480 ttctacccag cctggctcac agtgtcagag ggagcaaatg ccaccttcac ctgcagcttg    540
tccaactggt cggaggatct tatgctgaac tggaaccgcc tgagtccag caaccagact    600 gaaaaacagg ccgccttctg taatggtttg agccaacccg tccaggatgc ccgcttccag    660
atcatacagc tgcccaacag gcatgacttc cacatgaaca tccttgacac acggcgcaat    720
gacagtggca tctacctctg tggggccatc tccctgcacc ccaaggcaaa aatcgaggag    780
agccctggag cagagctcgt ggtaacagag agatctttta ctatcacggc tccaaaggac    840
ttgtacgtgg tggagtatgg cagcaacgtc acgatggagt gcagattccc tgtagaacgg    900
gagctggacc tgcttgcgtt agtggtgtac tgggaaaagg aagatgagca agtgattcag    960
tttgtggcag gagaggagga ccttaagcct cagcacagca acttcagggg gagagcctcg   1020
ctgccaaagg accagctttt gaagggaaat gctgcccttc agatcacaga cgtcaagctg   1080
caggacgcag gcgtttactg ctgcataatc agctacggtg gtgcggacta caagcgaatc   1140
acgctgaaag tcaatgcccc ataccgcaaa atcaaccaga gaatttccgt ggatccagcc   1200
acttctgagc atgaactaat atgtcaggcc gagggttatc cagaagctga ggtaatctgg   1260
acaaacagtg accaccaacc cgtgagtggg aagagaagtg tcaccacttc ccggacagag   1320
gggatgcttc tcaatgtgac cagcagtctg agggtcaacg ccacagcgaa tgatgttttc   1380
tactgtacgt tttggagatc acagccaggg caaaaccaca cagcggagct gatcatccca   1440
gaactgcctg caacacatcc tccacagaac agg                                1473
```

METHOD FOR ENHANCING IMMUNE RESPONSE IN THE TREATMENT OF INFECTIOUS AND MALIGNANT DISEASES

FIELD OF THE INVENTION

The present invention pertains to a new approach for the treatment of infectious and malignant diseases.

BACKGROUND OF THE INVENTION

Cytotoxic T-lymphocyte antigen-4 (CTLA-4) was found in 1987 to be a new member of the immunoglobulin superfamily, characterized by domains sharing key structural features with either the variable (V) or the constant (C) immunoglobulin domains (Brunet et al., Nature 328, 267-270). It was elucidated that CTLA-4 played a critical role in regulation of immune system (Keilholz, U., J Immunother 31, 431-439). CTLA-4 was reported to reduce T-cell activation by competing with CD28 for binding site of CD80/CD86 (Rudd et al., Immunol Rev 229, 12-26). Although CTLA-4 protects individuals from autoimmune diseases, it could also suppress anticancer immunity. To avoid the unwanted immune responses caused by CTLA-4 in cancer treatment, several approaches manipulating T-cell costimulatory pathway are being explored to enhance anticancer immune response. Therapy targeting CTLA-4 is one of the most advanced strategies and has revealed promising results in late stage clinical trials (Hodi et al., N Engl J Med 363, 711-723; Hodi, F. S., Asia Pac J Clin Oncol 6 Suppl 1, S16-23; Weber, J., Oncologist 13 Suppl 4, 16-25; and Ribas, A., Oncologist 13 Suppl 4, 10-15). One of the monoclonal antibodies against CTLA-4, ipilimumab, had been granted approval by the FDA in March of 2011 for treatment of metastatic melanoma. In addition to metastatic melanoma, CTLA-4 antibodies are currently undergoing numerous clinical trials for the treatment of malignancies including, pancreatic cancer, colorectal cancer, hepatocellular carcinoma, lymphoma, hormone refractory prostate cancer, ovarian cancer and acute myeloid leukemia.

Program death-1 (PD-1) is a member of the CD28 superfamily which triggers negative signaling pathway upon binding to its ligands, program death ligand 1 and 2 (PD-L1 and PD-L2) (Riley, J. L., Immunol Rev 229, 114-125). The interaction between PD-1 and its ligands leads to inhibition of proliferation, cytokine production, and cytolytic function of T-cell, thereby exhausting T-cell and suppressing its immune response. The PD-1/PD-L pathway plays an important role in tolerance and immunity. It protects tissues and organs from immune-mediated damage. However, this pathway has been shown to be utilized by pathogens of chronic infection and tumors to suppress antimicrobial and anticancer immunity. Given immune-modulating activity of PD-1/PD-L axis, therapeutics targeting this pathway has been developed for treatment of diseases ranging from infections, autoimmunity to cancers (Weber, J., Semin Oncol 37, 430-439).

Although progresses had been made to modify immune response against infectious and malignant diseases by targeting CTLA-4, PD-1/PD-L1/PD-L2 and other immune-modulating proteins, new approaches for anticancer and anti-infectious treatments by enhancing immunity while avoiding suppression of immune responses are still needed.

BRIEF SUMMARY OF THE INVENTION

The present invention provides a pharmaceutical composition for enhancing immune response in a subject under the treatment of an infectious or malignant disease, comprising a DNA construct fused with an expression vector and a pharmaceutically acceptable carrier, wherein the DNA construct comprises a polynucleotide sequence encoding any one selected from the group consisting of Cytotoxic T-lymphocyte antigen-4 (CTLA-4), programmed death-1 (PD-1), Programmed cell death 1 ligand 1 (PD-L1), fragments or functional variants thereof, and a combination thereof.

In another aspect, the present invention provides a pharmaceutical composition for enhancing immune response in a subject under the treatment of an infectious or malignant disease, comprising a recombinant polypeptide and a pharmaceutically acceptable carrier, wherein the recombinant polypeptide comprises a polypeptide sequence selected from the group consisting of the polypeptide sequence of CTLA-4, PD-1, PD-L1, fragments or functional variants thereof, and a combination thereof.

In yet another aspect, the invention provides a method for enhancing immune response in a subject under the treatment of an infectious or malignant disease, comprising administering a subject with a pharmaceutical composition which comprises a DNA construct fused with an expression vector and a pharmaceutically acceptable carrier, wherein the DNA construct comprises a polynucleotide sequence encoding any one selected from the group consisting of CTLA-4, PD-1, PD-L1, fragments or functional variants thereof, and a combination thereof.

In still another aspect, the invention provides a method for enhancing immune response in a subject under the treatment of an infectious or malignant disease, comprising administering a subject with a pharmaceutical composition which comprises a recombinant polypeptide and a pharmaceutically acceptable carrier, wherein the recombinant polypeptide comprises a polypeptide sequence selected from the group consisting of the polypeptide sequence of CTLA-4, PD-1, PD-L1, fragments or functional variants thereof, and a combination thereof.

BRIEF DESCRIPTION OF THE SEVERAL VIEWS OF THE DRAWINGS

For the purpose of illustrating the invention, there are shown in the drawings embodiments. It should be understood, however, that the invention is not limited to the preferred embodiments shown.

In the drawings:

FIG. 1a provides the DNA and amino acid sequences of pVAC-1-IL2ss-hCTLA-4-PLAP.

FIG. 1b provides the DNA and amino acid sequences of pVAC-1-IL2ss-mCTLA4-PLAP.

Figure 11A:
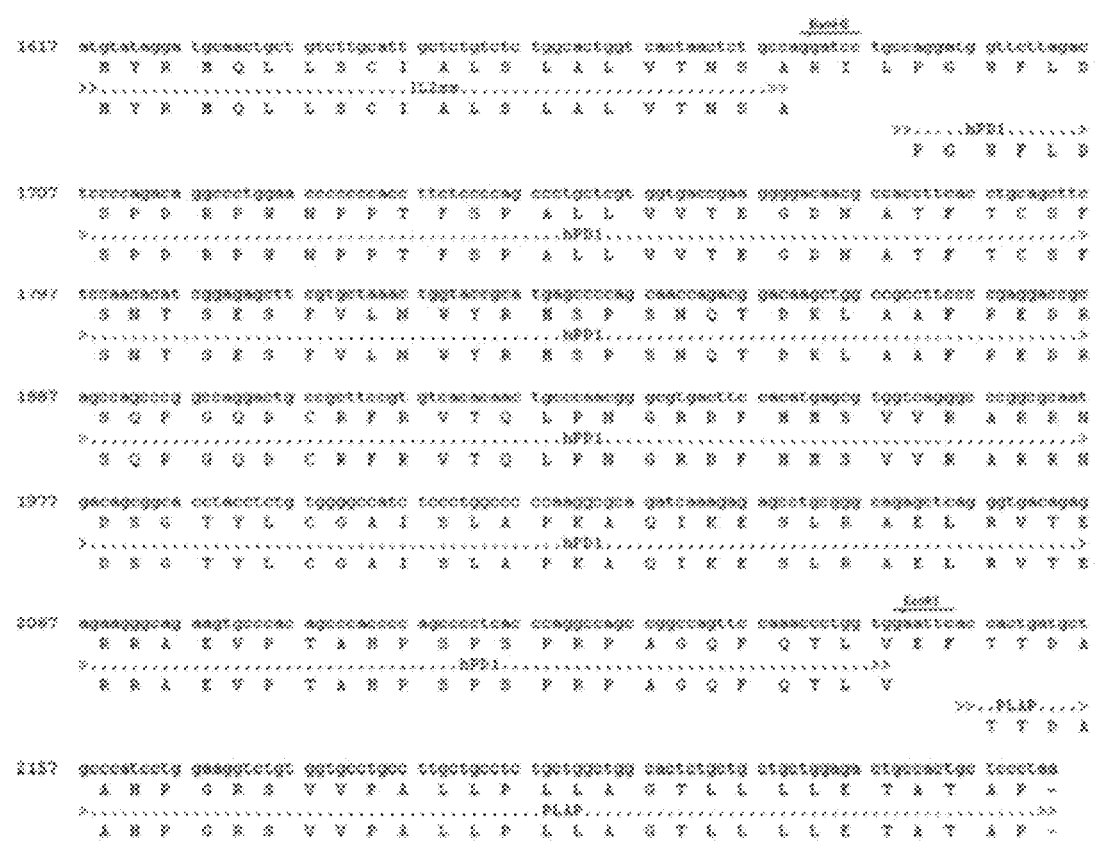
Figure 11B:
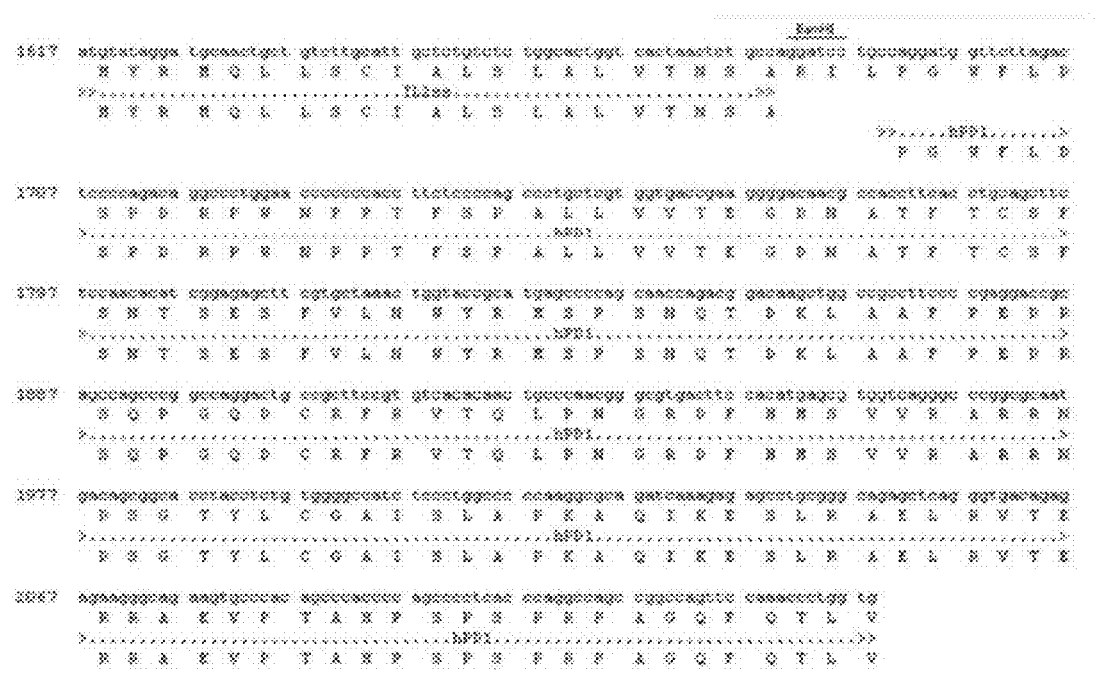

FIG. 11a provides the DNA and amino acid sequence of pVAC1-IL2ss-hPD-1(21-170aa)-PLAP (4167 bp); FIG. 11b provides the DNA and amino acid sequence of pVAC1-IL2ss-hPD-1(21-170aa) (4171 bp)

Figure 12A:
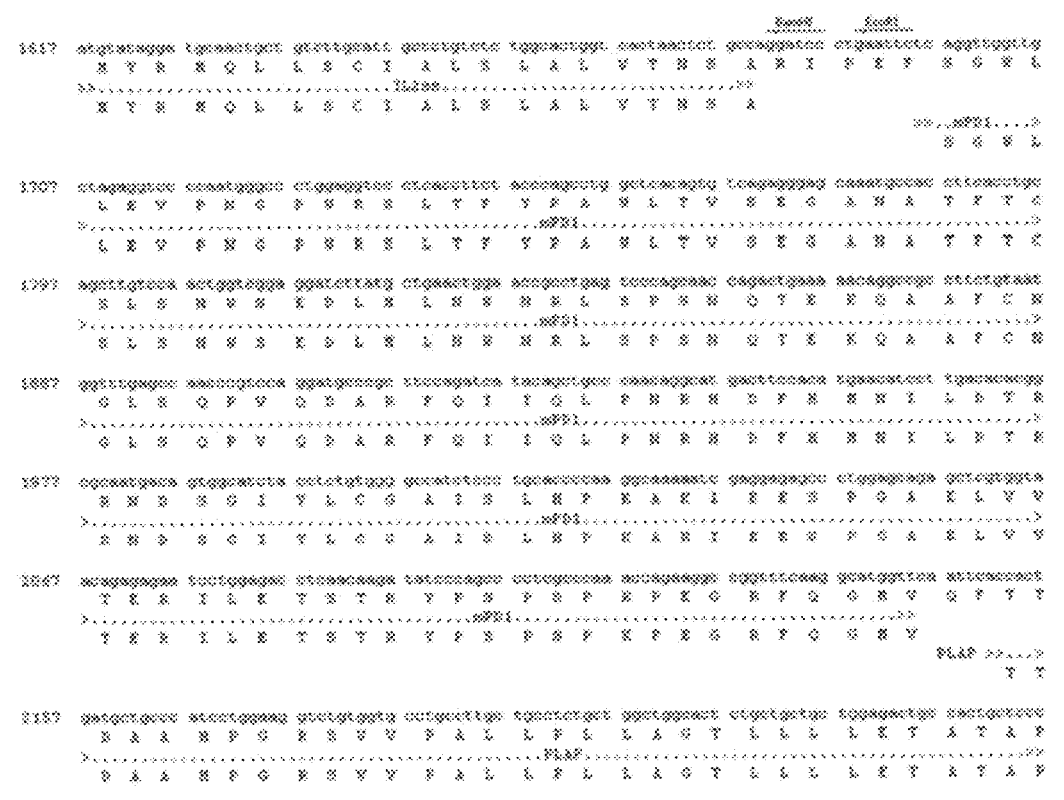
Figure 12B:
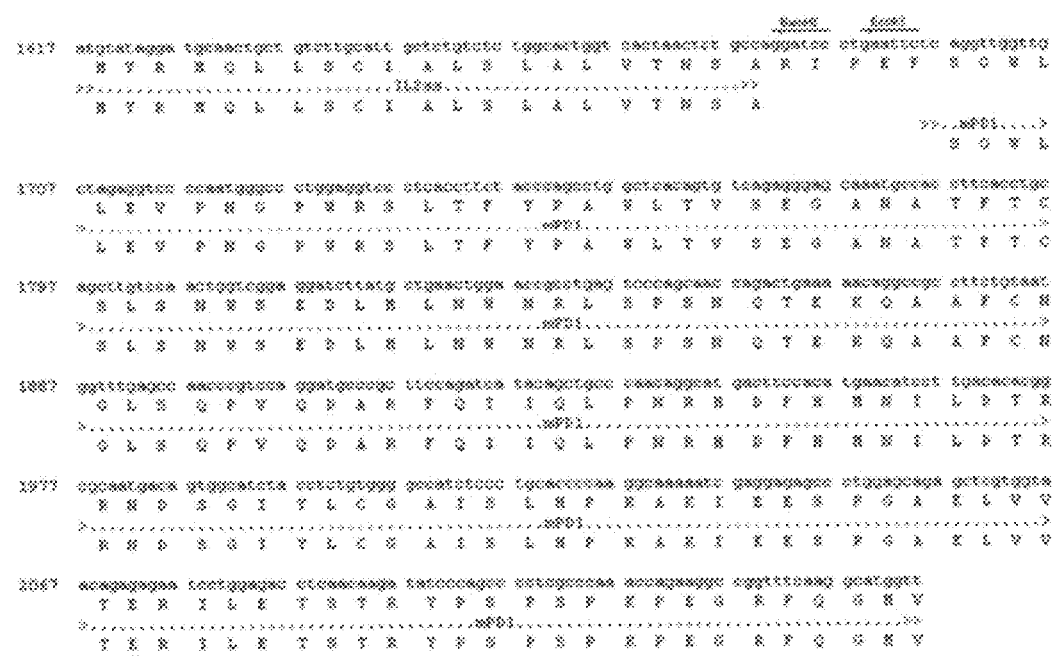
Figure 12C:
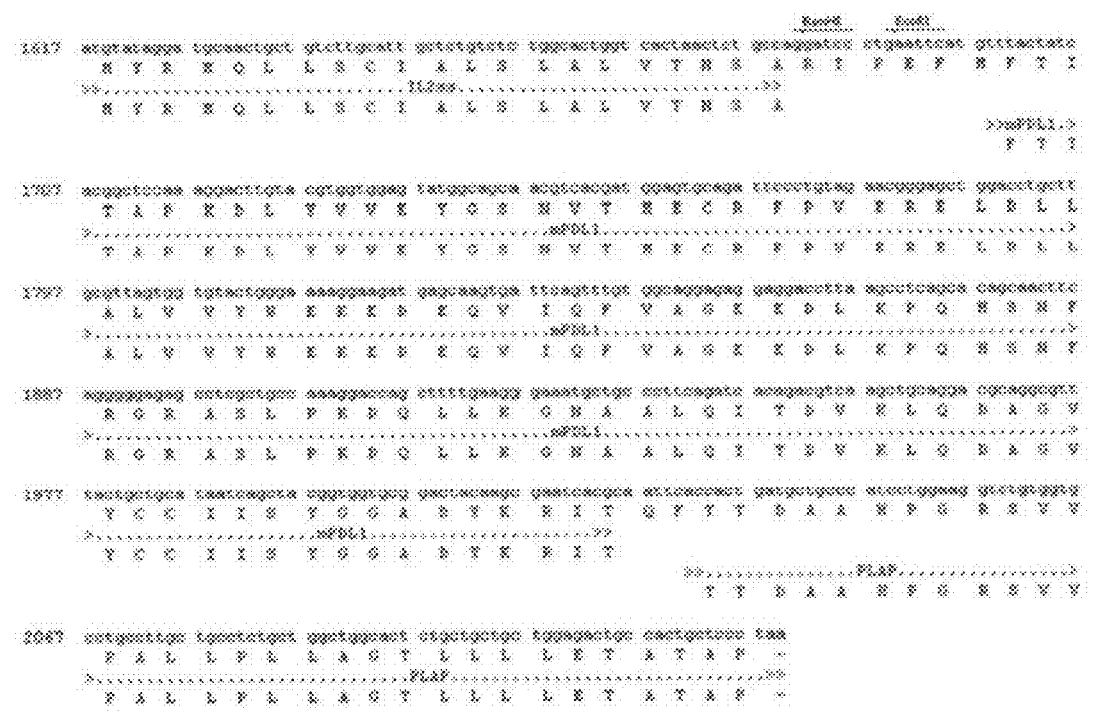
Figure 12D:
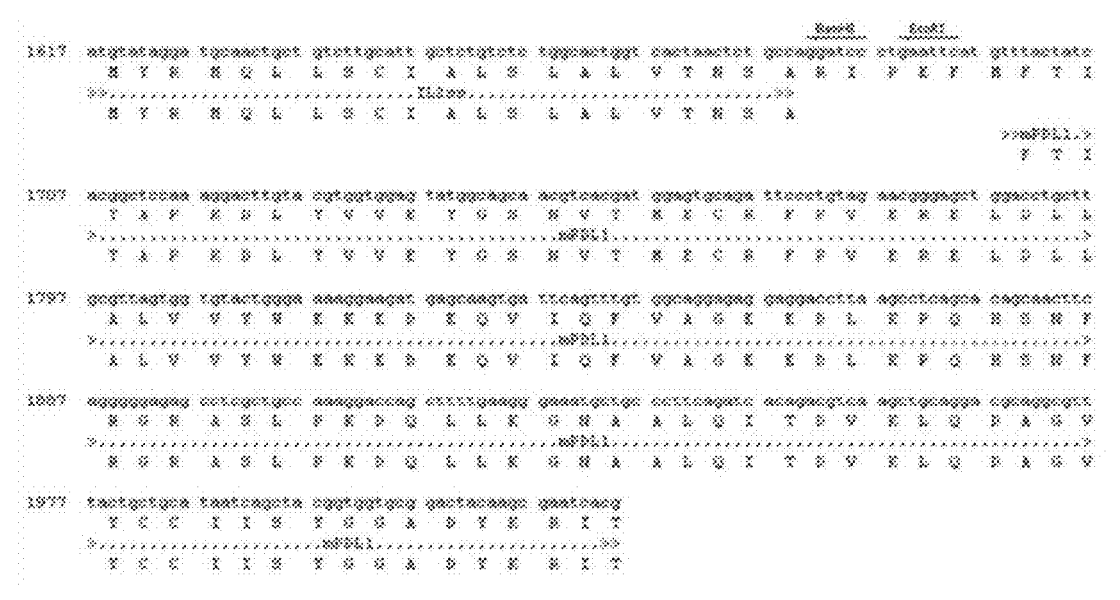

FIG. 12a provides the DNA and amino acid sequence of pVAC1-IL2ss-mPD-1(21-170aa)-PLAP (4173 bp); FIG. 12b provides the DNA and amino acid sequence of pVAC1-IL2ss-mPD-1(21-170aa) (4177 bp), FIG. 12c provides the DNA and amino acid sequence of pVAC1-IL2ss-mPD-L1(19-127aa)-PLAP (4053 bp); FIG. 12d provides the DNA and amino acid sequence of pVAC1-IL2ss-mPD-L1(19-127aa) (4057 bp)

FIG. 14a shows the titers of DNA vaccine induced antibodies against mPD-L1 (mPD-L1 antibody titers); and FIG. 14b shows the titers of DNA vaccine induced antibodies against and mCTLA-4 (mCTLA-4 antibody titers) as compared with those of control pVAC-1 vector are shown.

FIG. 15a shows the titers of DNA vaccine induced antibodies against mCTLA-4 (CTLA-4 antibody titers); FIG. 15b shows the titers of DNA vaccine induced antibodies against PD-1 (PD-1 antibody titers)

DETAILED DESCRIPTION OF THE INVENTION

Figure 2A:
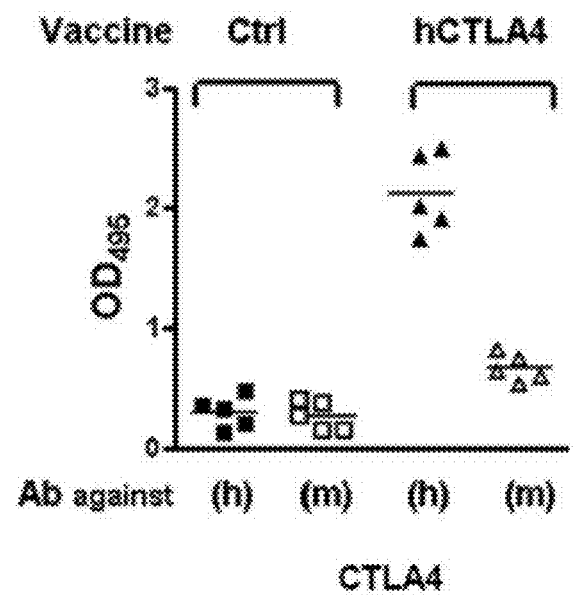
FIG. 2a shows the results of the mice immunized with pVAC-1-IL2ss-hCTLA-4-PLAP generating antibody against both human and murine CTLA-4.

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides, such as recombinant polynucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "poly nucleotide encoding an amino acid sequence" includes all polynucleotides that are degenerate versions of each other and that encode the same amino acid sequence. Polynucleotides that encode proteins and RNA may include introns.

The term "recombinant polynucleotide" refers to a polynucleotide having sequences that are not naturally joined together. A recombinant polynucleotide may be present in the form of a vector. "Vectors" may contain a given nucleotide sequence of interest and a regulatory sequence. Vectors may be used for expressing the given nucleotide sequence or maintaining the given nucleotide sequence for replicating it, manipulating it or transferring it between different locations (e.g., between different organisms). Vectors can be introduced into a suitable host cell for the above mentioned purposes.

Examples of vectors include, but are not limited to, plasmids, cosmids, phages, YACs, or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence, a start codon, a replication origin, enhancers, an operator sequence, a secretion signal sequence (e.g., IL2 signal peptide) and other control sequence. Preferably, vectors may further contain a marker sequence (e.g., an antibiotic resistant marker sequence) for the subsequent screening procedure.

The term "polypeptide" refers to a molecule or a polymer composed of amino acid residues linked via peptide bonds. Polypeptide can be synthesized, for example, using an automated polypeptide synthesizer. The term "protein" typically refers to large polypeptides. The term "peptide" typically refers to short polypeptides.

Amino acids can be expressed by three letters or one letters. Table 1 lists standard amino acid abbreviations.

TABLE 1

Standard amino acid abbreviations

| Amino Acid | 3-Letter | 1-Letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "vaccine" refers to an agent or composition containing an active component effective to induce a therapeutic degree of immunity in a subject against a certain pathogen or disease. Traditionally, the active component of a vaccine is a polypeptide derived from a pathogen which is the target of the vaccine. The term "DNA vaccine" refers to a vaccine wherein the active component is DNA. The term "protein vaccine" refers to a vaccine wherein the active component is polypeptide.

The term "pharmaceutical composition" refers to a composition suitable for pharmaceutical use in a subject. A pharmaceutical composition comprises an effective amount of an active agent and a pharmaceutically acceptable carrier. The term "effective amount" refers to that amount of an agent effective to produce the intended result, such as the immune response in this invention. The term "pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). The term "adjuvant" refers to a pharmacological or immunological agent that modifies the effect of other agents (e.g., drugs, vaccines) while having few if any direct effects when given by itself. They are often included in vaccines to enhance the recipient's immune response to a supplied antigen while keeping the injected foreign material at a minimum.

A "subject" is a human or non-human mammal. Non-human mammals include, but are not limited to, primates, ungulates, canines and felines.

A "naked DNA" refers to a DNA construct (for administration to a subject) which is not coupling to liposome.

A "fragment" of a polypeptide (or protein) refers to a polypeptide that has an amino-terminal and/or carboxy-terminal deletion, but where the remaining amino acid sequence is identical to the corresponding positions in the naturally-occurring sequence deduced, for example, from a full-length DNA sequence. Fragments typically are at least 10 amino acids long, preferably are 10-50 amino acids long, more preferably are 50-100 amino acids long, and even more preferably are more than 100 amino acids long.

A "functional variant" of a polypeptide (or protein) refers to is a polypeptide which contains one or more modifications to the primary amino acid sequence of the polypeptides (or proteins) of the present invention while retaining the immunostimulatory effect disclosed herein. If a functional variant of a polypeptide (or protein) of the present invention involves an amino acid substitution, conservative amino acid substitutions typically will be preferred, i.e., substitutions which retain a property of the original amino acid such as size, charge, hydrophobicity, conformation, etc. Examples of conservative substitutions of amino acids include substitutions made among amino acids within the following groups: (1) M, I, L, V; (2) F, Y, W; (3) K, R, H; (4) A, G; (5) S, T; (6) Q, N; and (7) E, D. Other suitable substitutions are easily established by the person of skill and may additionally be determined by reference to publications such as Voet, *Biochemistry*, Wiley, 1990; Stryer *Biochemistry* 4$^{th}$ Ed., Freeman N.Y., 1995; *Peptide Chemistry. A Practical Textbook*, 2nd ed., Miklos Bodanszky, Springer-Verlag, Berlin, 1993; *Principles of Peptide Synthesis*, 2nd ed., Miklos Bodanszky, Springer-Verlag, Berlin, 1993; *Chemical Approaches to the Synthesis of Peptides and Proteins*, P. Lloyd-Williams, F. Albericio, E. Giralt, CRC Press, Boca Raton, 1997; *Bioorganic Chemistry: Peptides and Proteins*, S. M. Hecht, Ed., Oxford Press, Oxford, 1998; *Synthetic Peptides: A User's Guide*, Gregory A. Grant (Editor), Oxford University Press, 2002, and the like, all of which are incorporated by reference herein.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol and combinations thereof.

The present invention provides a pharmaceutical composition for enhancing immune response in a subject under the treatment of an infectious or malignant disease, comprising a DNA construct fused with an expression vector and a pharmaceutically acceptable carrier, wherein the DNA construct comprises a polynucleotide sequence encoding any one selected from the group consisting of Cytotoxic T-lymphocyte antigen-4 (CTLA-4), programmed death-1 (PD-1), Programmed cell death 1 ligand 1 (PD-L1), fragments or functional variants thereof, and a combination thereof.

According to one embodiment, the pharmaceutical composition of the invention comprises a DNA construct comprising a polynucleotide sequence encoding CTLA-4 fused to pVAC-1 vector, and said composition provide a protective effect on tumor growth in both melanoma and renal cell carcinoma models.

It is supposed that simultaneously blocks CTLA-4 and PD-1 and/or PD-L1 should further enhance immunity against pathogen and cancer cells. According to certain embodiments, the pharmaceutical composition of the invention is capable of inducing immunity specific for CTLA-4 and PD-1 and/or PD-L1. In some embodiments, the pharmaceutical composition of the invention comprises a DNA construct encoding both CTLA-4 and PD-1 fused to a vector, e.g., pVAC-1-IL2ss-CTLA4-PD-1-PLAP and pVAC-1-IL2ss-CTLA4-PD-1. In some embodiments, the pharmaceutical composition of the invention comprises a DNA construct encoding both CTLA-4 and PD-L1, e.g., pVAC-1-IL2ss-CTLA4-PD-L1-PLAP and pVAC-1-IL2ss-CTLA4-PD-L1. In these embodiments, antibody titers against both of the antigens were elevated in experimental mice, and tumor growths therein were greatly suppressed.

According to the invention, the DNA vaccine has several advantages over the existing therapeutics targeting similar pathways related to CTLA-4, PD-1, PD-L1 and other immune-modulating pathways, such as using antibodies against CTLA-4, PD-1, PD-L1 and other immune-modulating molecules. For example, the mass production of the DNA construct is much easier and less costly than that of antibodies. Moreover, our CTLA-4-PD-1, CTLA-4-PD-L1 and CTLA-4-PD-1-PD-L1 fusion DNA vaccines represent a method to deliver one single therapy for simultaneous inhibition of these two or three important drug targets. It will be much more difficult to administer multiple antibodies specific for CTLA-4, PD-1, or PD-L1 to accomplish potentially more potent immunity given the cost of delivering multiple antibodies. Besides, regulatory issues regarding the administration of two experimental drugs will hinder the early onset of trial with combinational therapy. The fusion gene DNA vaccines strategy could offer a way to simultaneously manipulate multiple pathways of immune system without having to administer more several experimental therapeutics, which is infeasible economically and not allowed by regulatory bodies of most countries.

In other embodiments of the present invention, more DNA constructs are cloned as DNA vaccines, which can be composed of more than one DNA sequences (such as those coding for CTLA-4, PD-1, PD-L1, or others) of human, murine, human and murine chimeric, other species, or chimera of human and other species. The DNA sequences may be those encoding the proteins involving functions of immune system, or pathogenesis of infectious diseases, or tumorigenesis of malignancies, such as CTLA-4, PD-1, PD-L1, fragments or functional variants thereof, and a combination thereof.

In another aspect, the invention provides a pharmaceutical composition for enhancing immune response in a subject under the treatment of an infectious or malignant disease, comprising a recombinant polypeptide and a pharmaceutically acceptable carrier, wherein the recombinant polypeptide comprises a polypeptide sequence selected from the group consisting of the polypeptide sequence of CTLA-4, PD-1, PD-L1, fragments or functional variants thereof, and a combination thereof.

According to one embodiment, the pharmaceutical composition of the invention comprises a recombinant polypeptide comprising the polypeptide sequence of CTLA-4 and PD-1, CTLA-4 and PD-L1, or CTLA-4 and PD-1 and PD-L1, and said composition provide a protective effect on tumor growth in both melanoma and renal cell carcinoma models.

In yet another aspect, the invention provides a method for enhancing immune response in a subject under the treatment of an infectious or malignant disease, comprising administering a subject with the pharmaceutical composition as described herein.

In embodiments of the instant invention, the subject is treated with an anti-infection or anti-cancer drug causing a stimulation of immune response in the subject. As one example of the present invention, the subject is under the treatment of a malignant disease.

According to the present invention, the malignant disease may be selected from the group consisting of metastatic melanoma, pancreatic cancer, colorectal cancer, hepatocellular carcinoma, lymphoma, hormone refractory prostate cancer, ovarian cancer, acute myeloid leukemia, and non-small cell lung cancer.

The present invention is further illustrated by the following examples, which are provided for the purpose of demonstration rather than limitation.

EXAMPLE 1: CLONING OF DNA VACCINE CONSTRUCTS

Figure 1A:
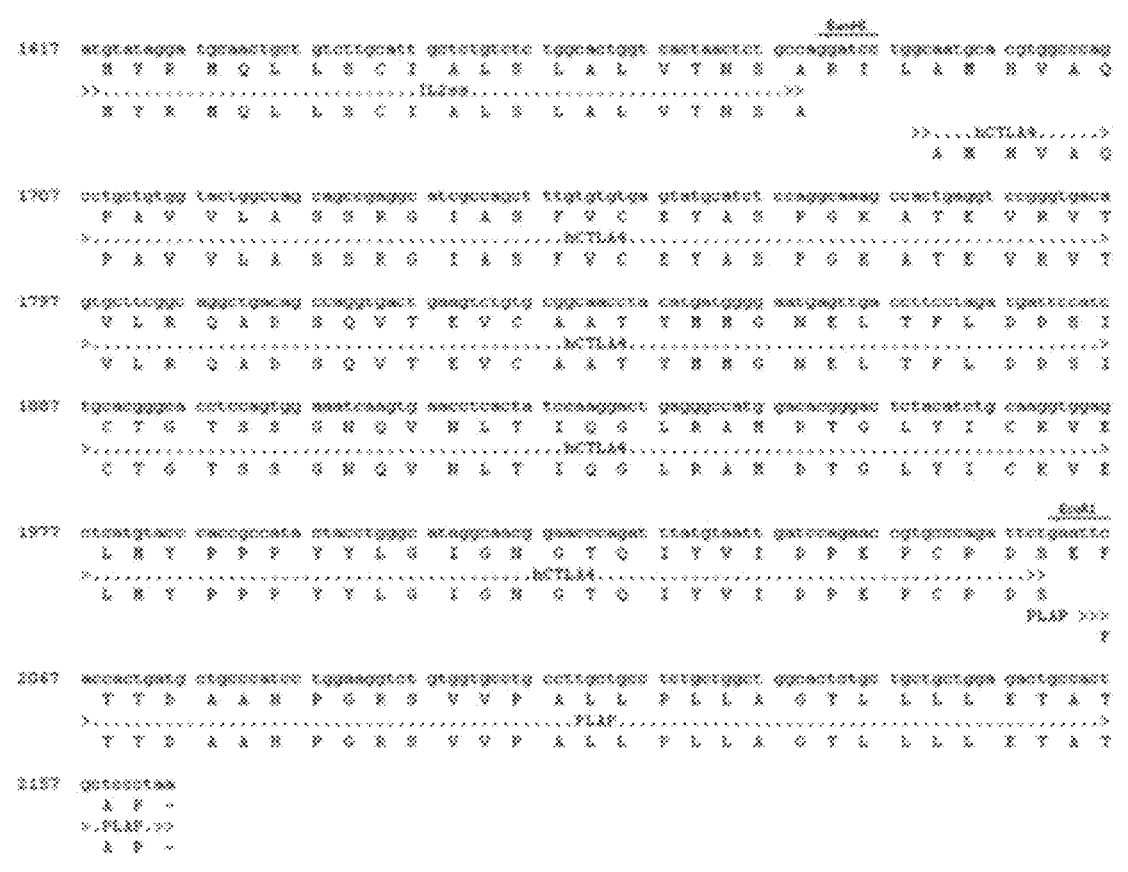
Figure 1B:
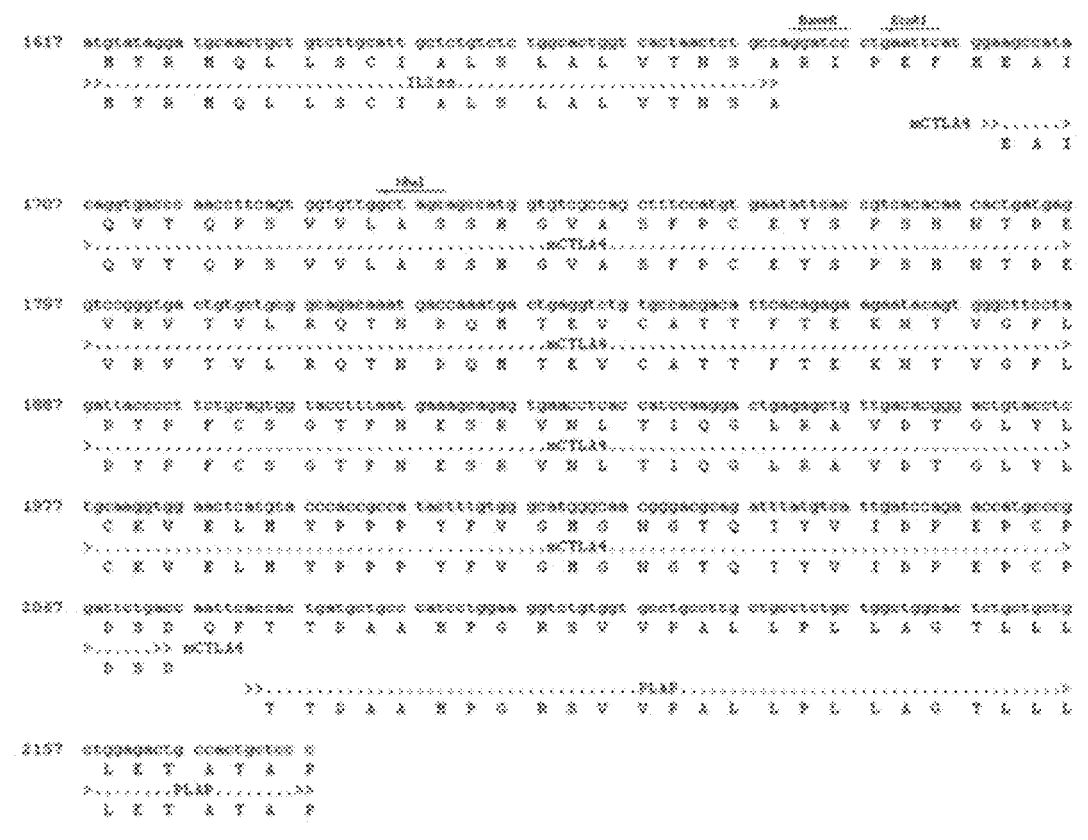
Figure 10:
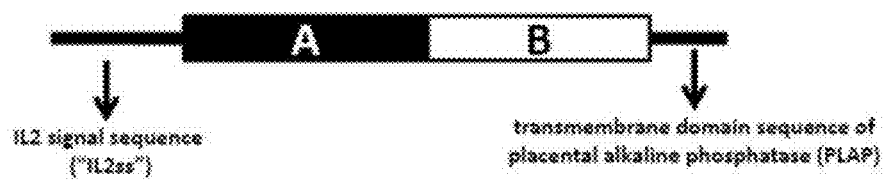
FIG. 10 provide the cloning strategy for vaccines targeting immune-modulating proteins either as membrane-tethered (a) or secreted (b) proteins in the presence or absence of transmembrane domain sequence of placental alkaline phosphatase (PLAP), respectively. DNA sequences of "A" and "B" regions shown in FIG. 10 may be that encoding any one selected from the group consisting of CTLA-4, PD-1, PD-L1, fragments or functional variants thereof, and a combination thereof.
Figure 10:
Figure 11C:
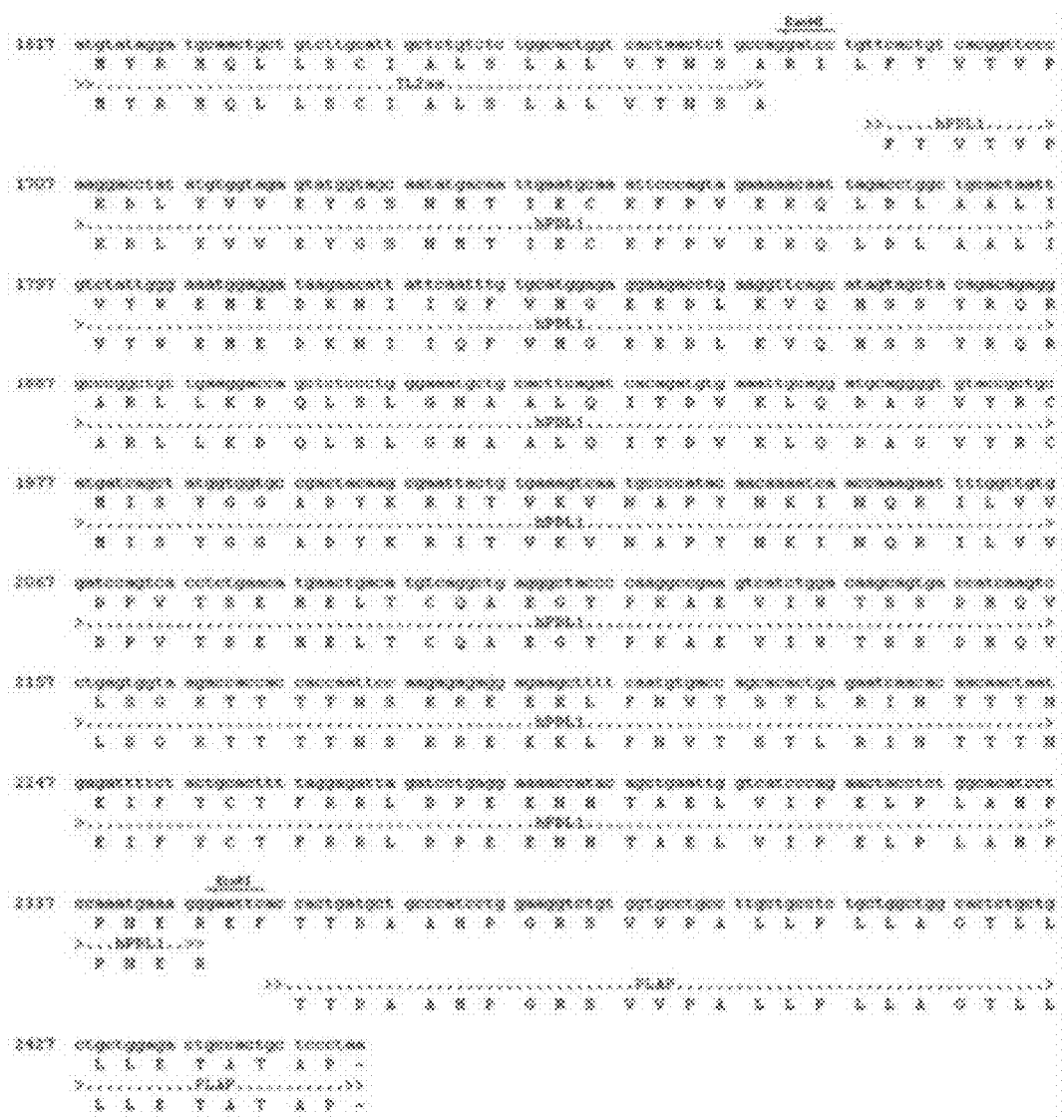
FIG. 11c provides the DNA and amino acid sequence of pVAC1-IL2ss-hPD-L1(19-238aa)-PLAP (4377 bp)
Figure 11D:
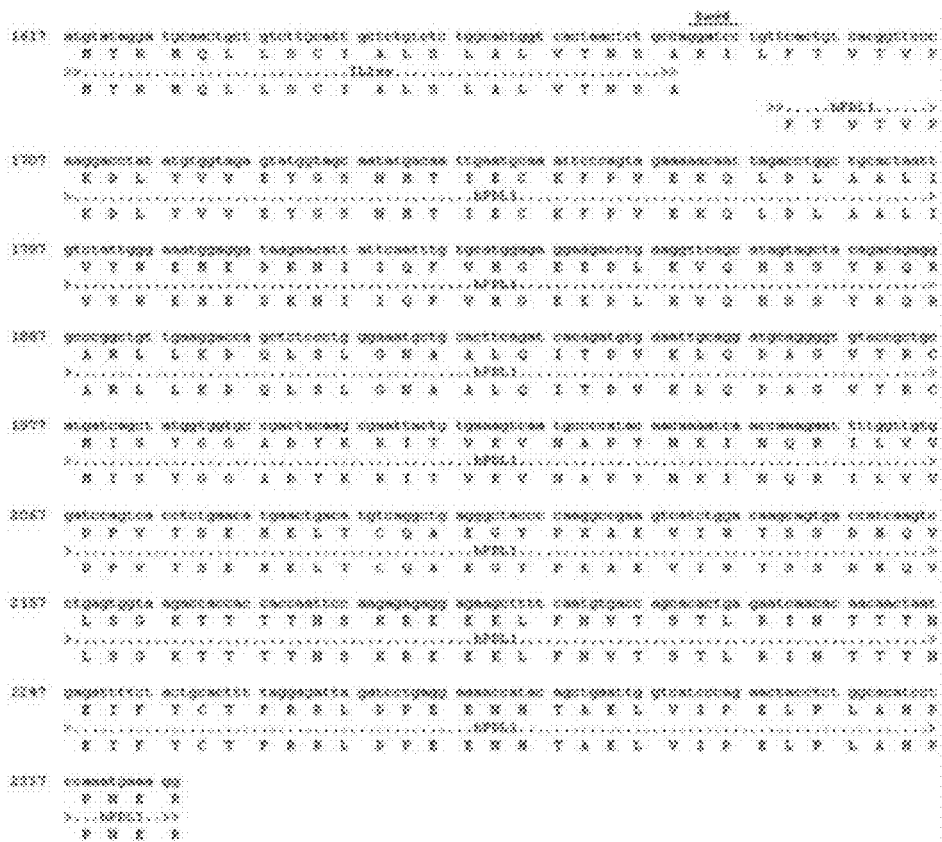
FIG. 11d provides the DNA and amino acid sequence of pVAC1-IL2ss-hPD-L1(19-238aa) (4381 bp)
Figure 11E:
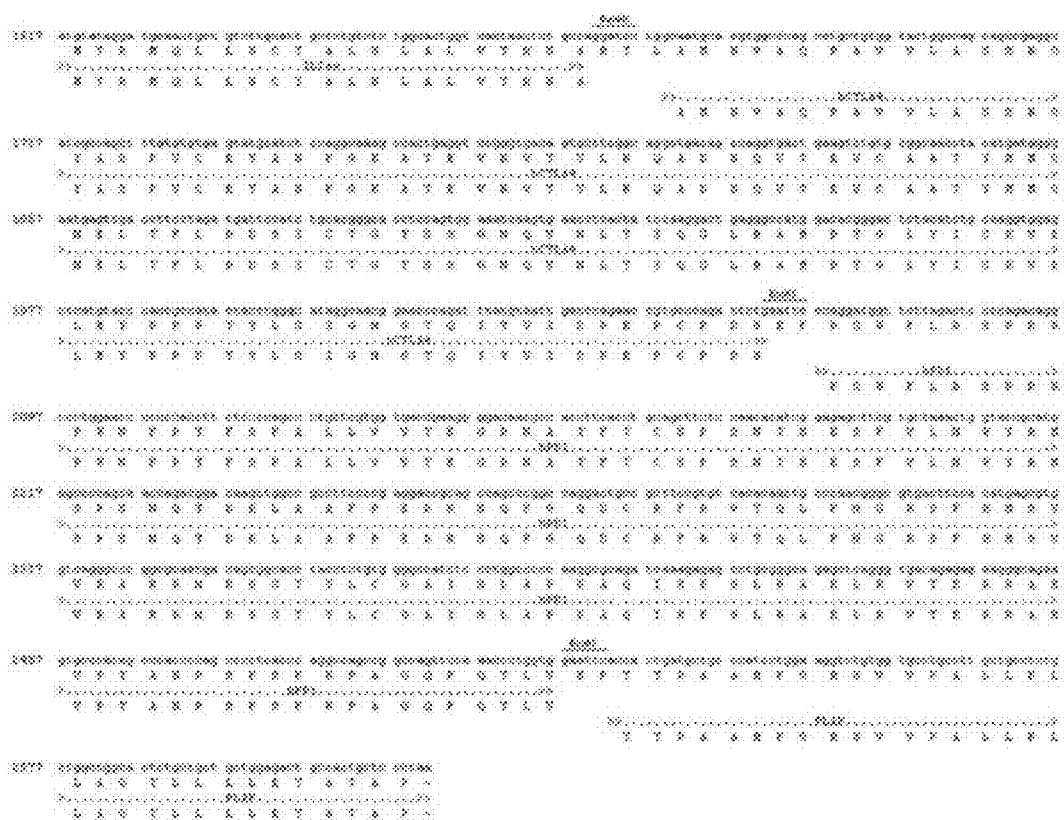
FIG. 11e provides the DNA and amino acid sequence of pVAC1-IL2ss-hCTLA4-hPD-1(21-170aa)-PLAP (4545 bp)
Figure 11F:
FIG. 11f provides the DNA and amino acid sequence of pVAC1-IL2ss-hCTLA4-hPD-1(21-170aa) (4443 bp)
Figure 11G:
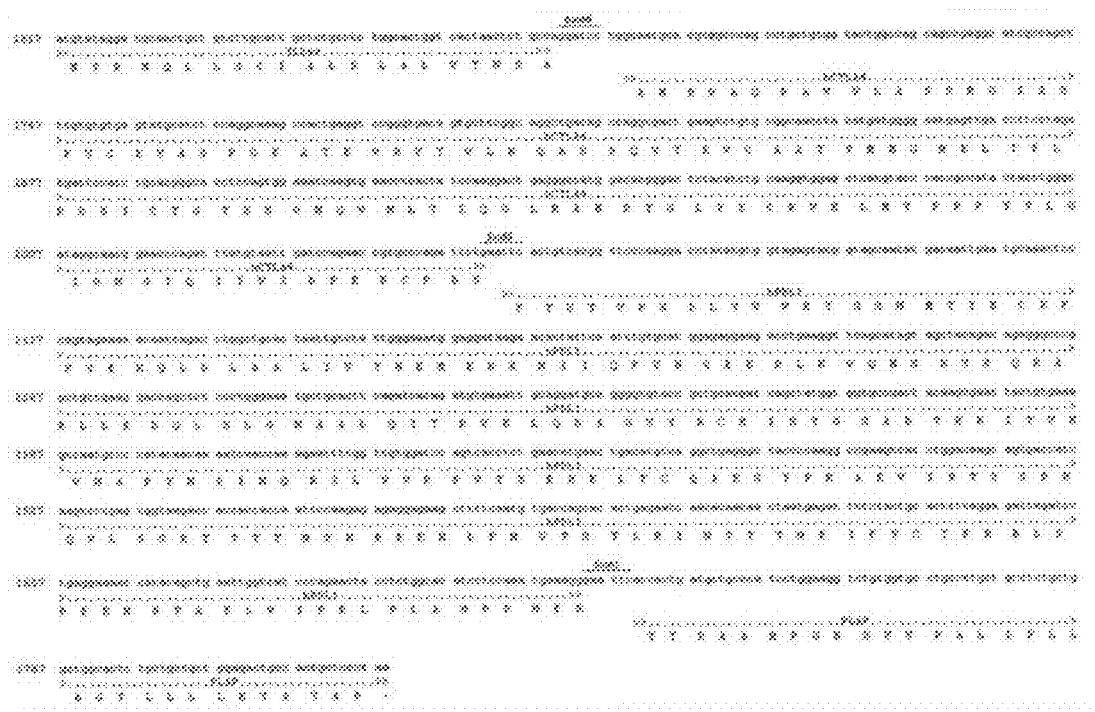
FIG. 11g provides the DNA and amino acid sequence of pVAC1-IL2ss-hCTLA4-hPD-L1(19-238aa)-PLAP (4752 bp)
Figure 11H:
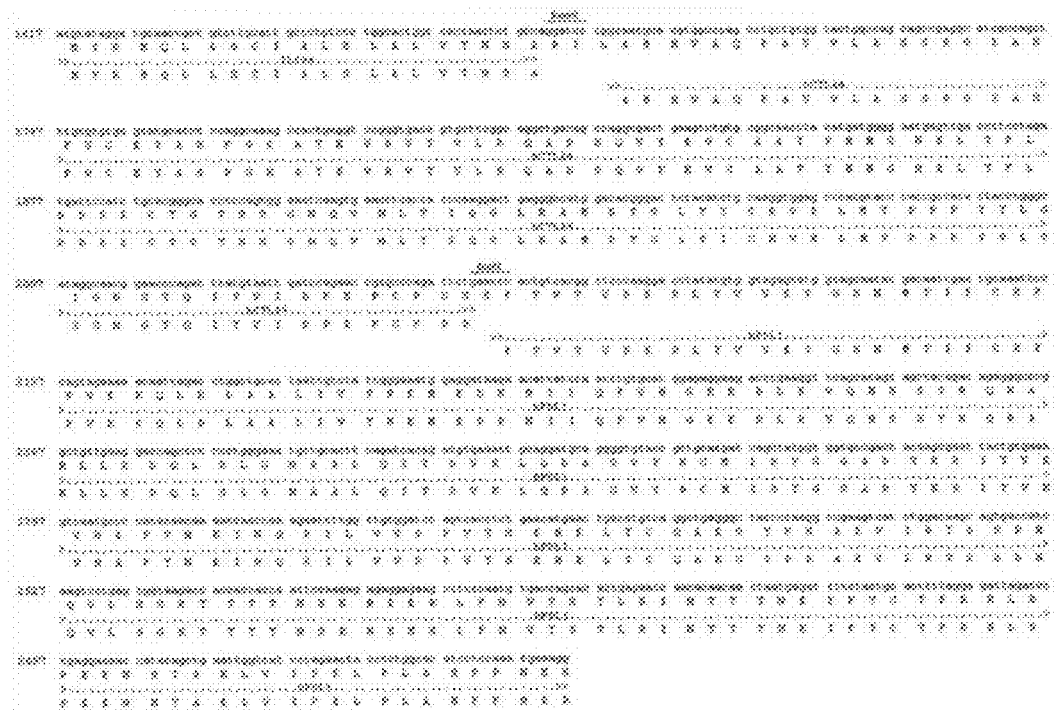
FIG. 11h provides the DNA and amino acid sequence of pVAC1-IL2ss-hCTLA4-hPD-L1(19-238aa)(4650 bp).
Figure 12E:
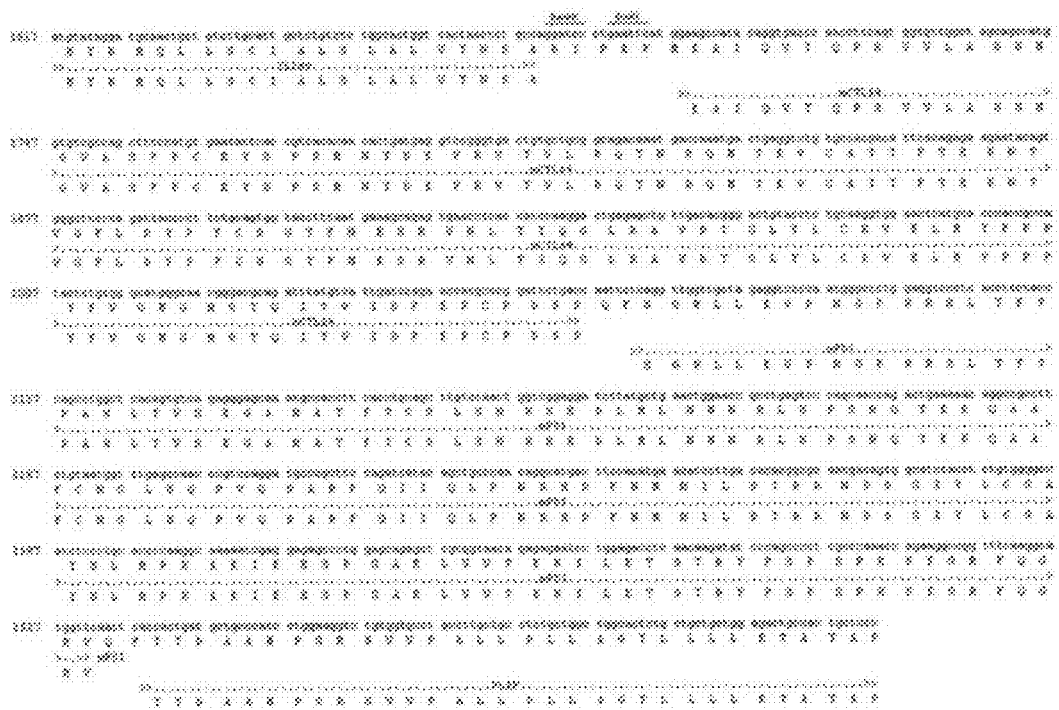
FIG. 12e provides the DNA and amino acid sequence of pVAC1-IL2ss-mCTLA4-mPD-1(21-170aa)-PLAP (4560 bp)
Figure 12F:
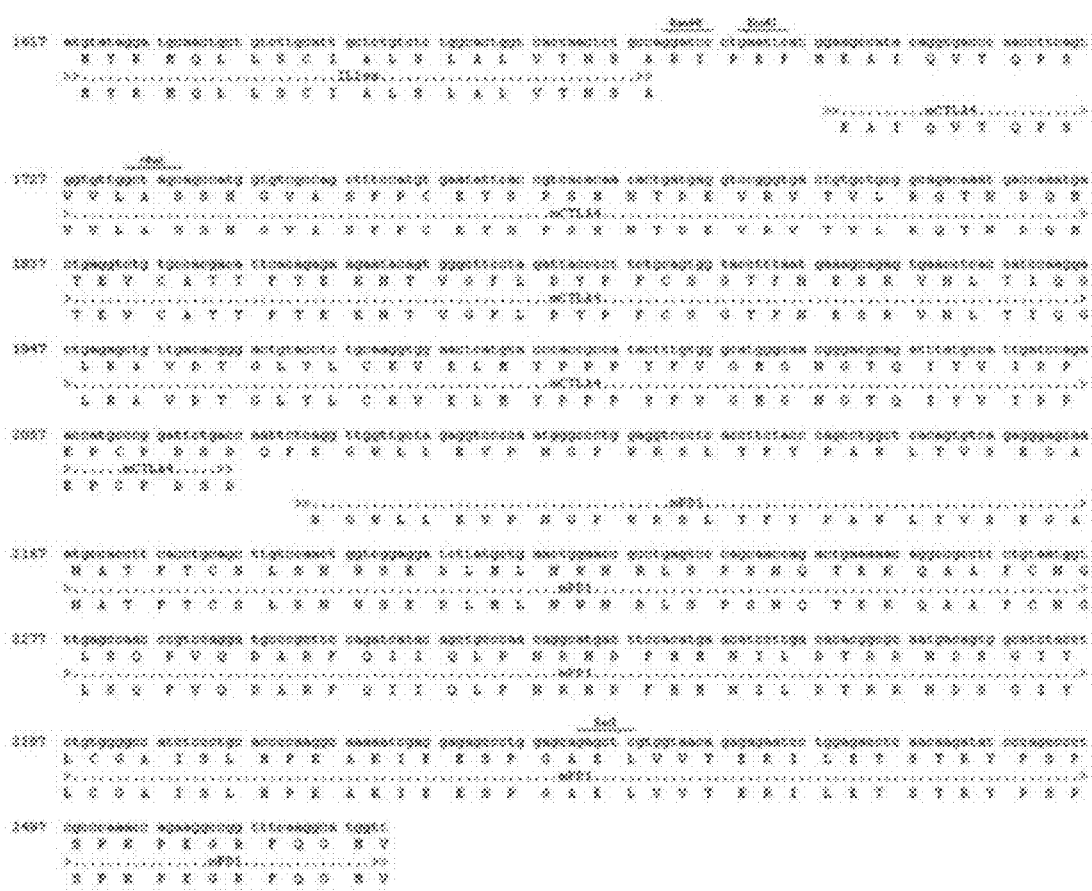
FIG. 12f provides the DNA and amino acid sequence of pVAC1-IL2ss-mCTLA4-mPD-1 (21-170aa) (4458 bp)
Figure 12G:
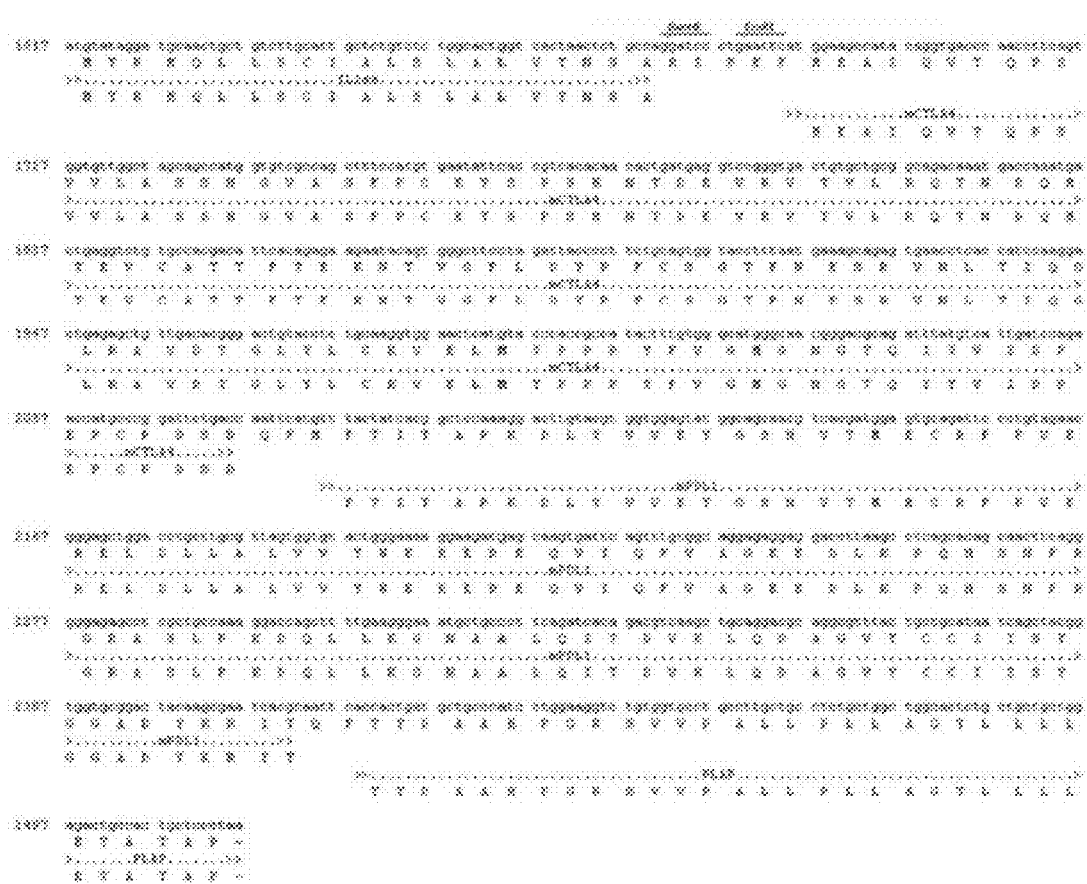
FIG. 12g provides the DNA and amino acid sequence of pVAC1-IL2ss-mCTLA4-mPD-1 (19-127aa)-PLAP (4440 bp)
Figure 12H:
FIG. 12h provides the DNA and amino acid sequence of pVAC1-IL2ss-mCTLA4-mPD-L1(19-127aa) (4338 bp).
Figure 13A:
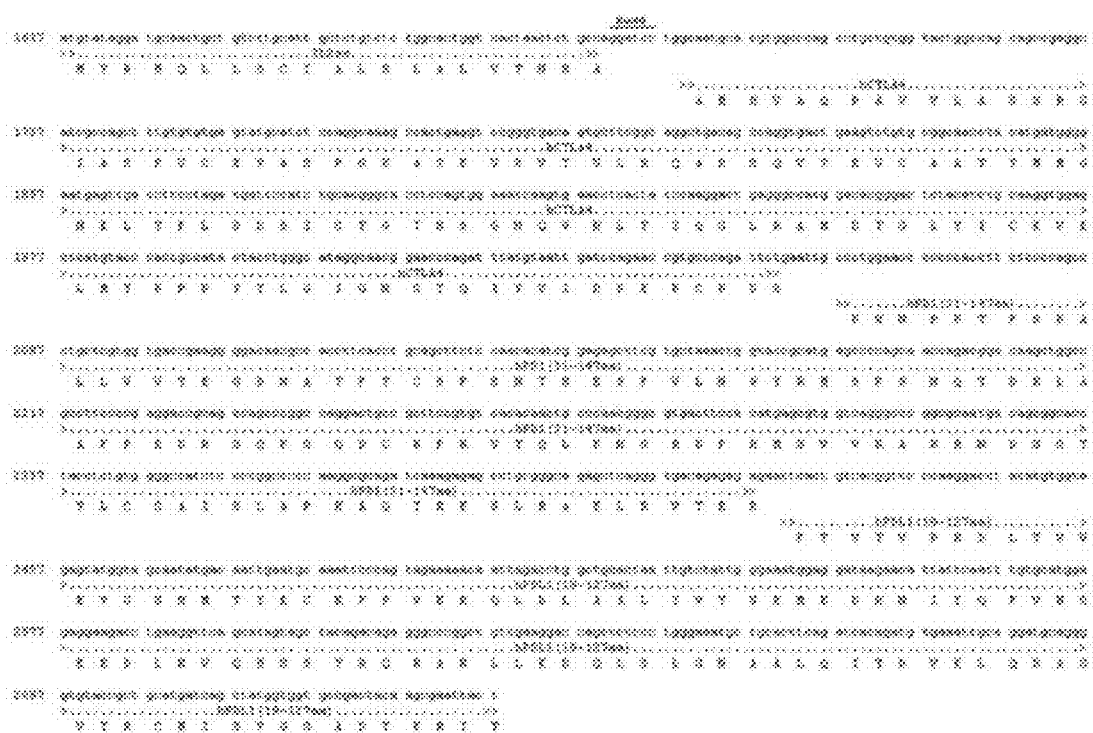
FIG. 13a provide the DNA and amino acid sequence of pVAC1-IL2ss-hCTLA4-hPD1(31-147aa)-hPDL1(19-127aa)
Figure 13B:
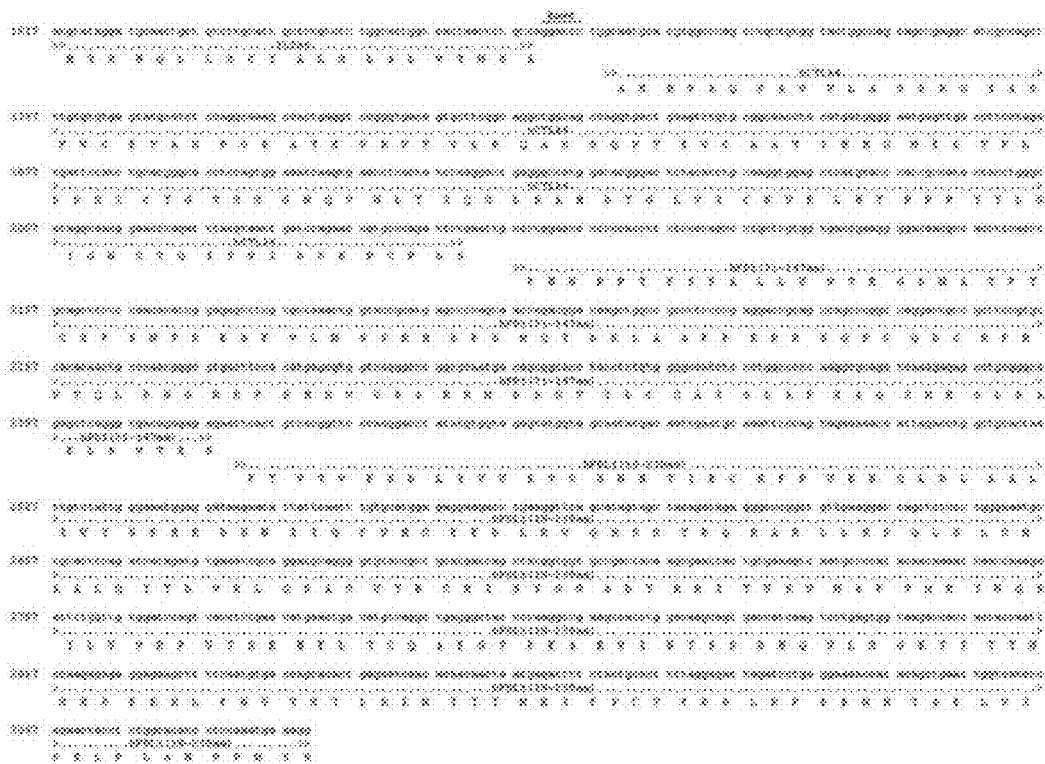
FIG. 13b provides the DNA and amino acid sequences of pVAC1-IL2ss-hCTLA4-hPD1(31-147aa)-hPDL1(19-238aa)
Figure 13C:
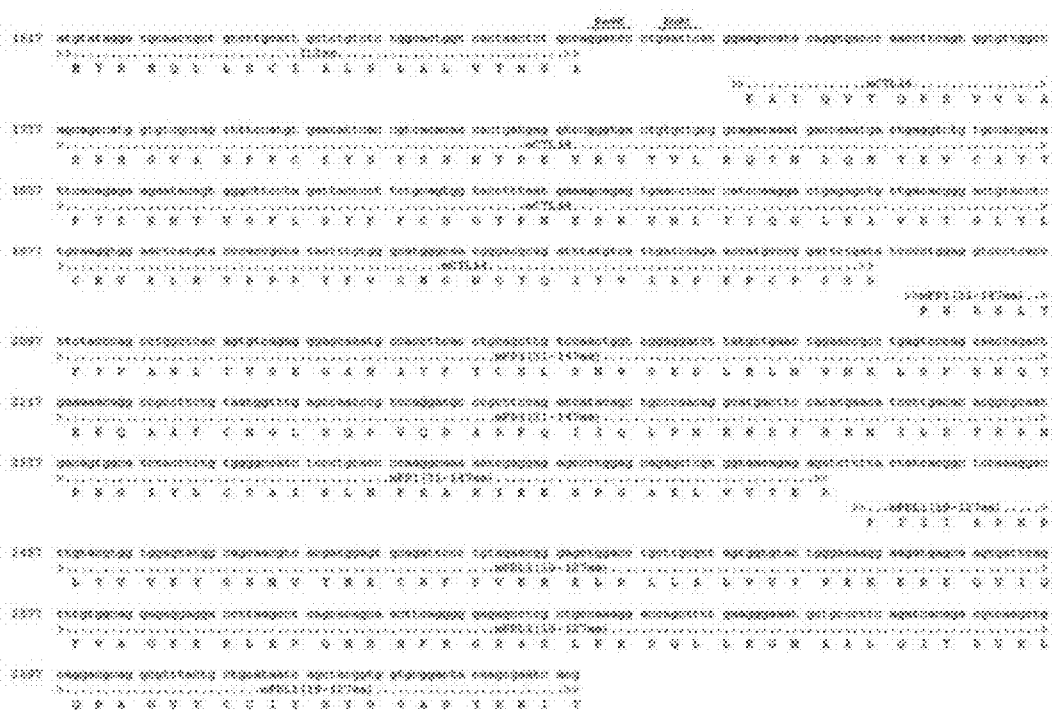
FIG. 13c provides the DNA and amino acid sequences of pVAC1-IL2ss-mCTLA4-mPD1(31-147aa)-mPDL1(19-127aa)
Figure 13D:
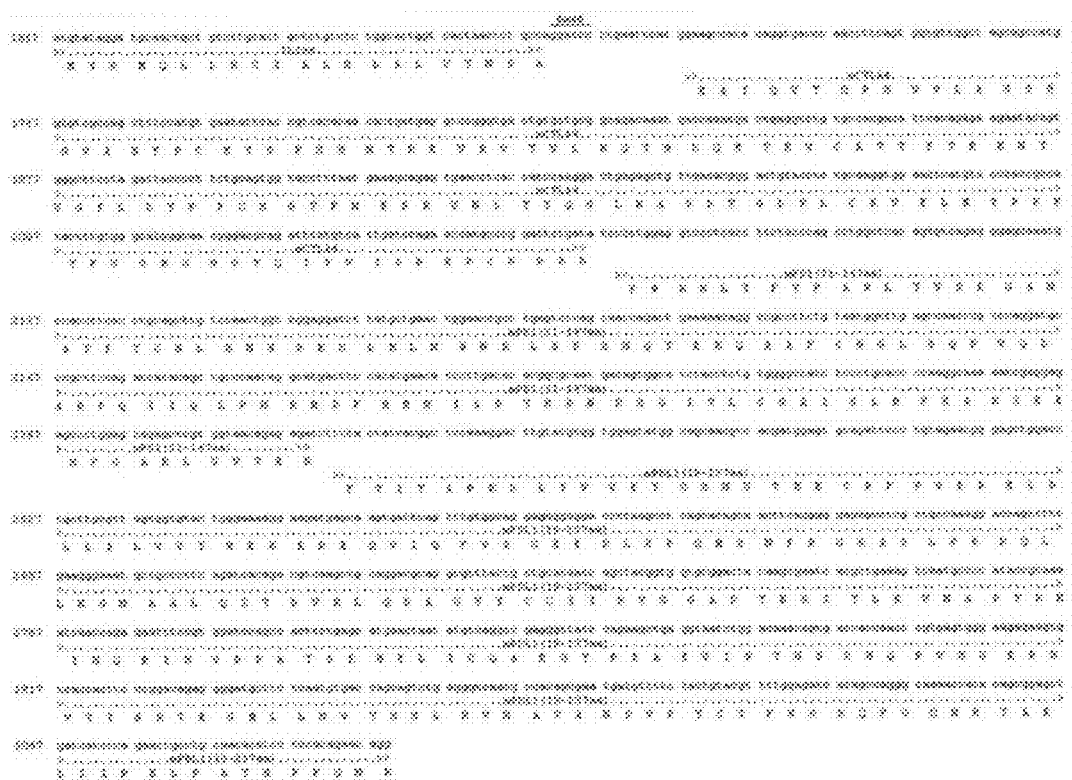
FIG. 13d provides the DNA and amino acid sequences of pVAC1-IL2ss-mCTLA4-mPD1(31-147aa)-mPDL1(19-237aa).

To construct DNA vaccines of CTLA-4, the sequence of either human or murine CTLA-4 is cloned and fused with IL2 secretion signal sequence (IL2ss) and a transmembrane domain sequence of placental alkaline phosphatase (PLAP), at N- and C-terminus, respectively, into a mammalian expression plasmid, pVAC-1. The DNA sequences of pVAC1-IL2ss-hCTLA-4-PLAP (SEQ ID NO: 1) and pVAC1-IL2ss-mCTLA-4-PLAP (SEQ ID NO: 2) as obtained are listed in FIGS. 1a and 1b. The DNA vaccines specific for individual human or murine PD-1 or PD-L1, and human or murine fusion gene constructs composed of CTLA-4 and PD-1 and/or PD-L1 with or without transmembrane domain of PLAP at the C-terminus were constructed as shown in FIG. 10 and below:
(1) pVAC-1-IL2ss-hPD-L1 (containing DNA sequence encoding human PD-L1);
(2) pVAC-1-IL2ss-hPD-1 (containing DNA sequence encoding human PD-1);
(3) pVAC-1-IL2ss-hCTLA4-hPD-L1 (containing DNA sequence encoding human CTLA-4 and PD-L1);
(4) pVAC-1-IL2ss-hCTLA4-hPD-1 (containing DNA sequence encoding human CTLA-4 and PD-1);
(5) pVAC-1-IL2ss-hCTLA4-hPD-1-hPD-L1 (containing DNA sequence encoding human CTLA-4, PD-1 and PD-L1);
(6) pVAC-1-IL2ss-mPD-L1 (containing DNA sequence encoding mouse PD-L1);
(7) pVAC-1-IL2ss-mPD-1 (containing DNA sequence encoding mouse PD-1);
(8) pVAC-1-IL2ss-mCTLA4-mPD-L1 (containing DNA sequence encoding mouse CTLA-4 and PD-L1);
(9) pVAC-1-IL2ss-mCTLA4-mPD-1 (containing DNA sequence encoding mouse CTLA-4 and PD-1); and
(10) pAC-1-IL2ss-mCTLA4-mPD-1-mPD-L1 (containing DNA sequence encoding mouse CTLA-4, PD-1 and PD-L1).

EXAMPLE 2: CONSTRUCTS AND PURIFICATION OF RECOMBINANT POLYPEPTIDES

To construct recombinant polypeptides of CTLA-4-PD-1 and CTLA-4-PD-L1, murine CTLA-4 fused with PD-1 or PD-L1 is cloned into pET56, an *E. coli.* expression vector. The protein sequence of mCTLA-4-mPD-1-His$_6$ and mCTLA-4-mPD-L1-His$_6$ as purified using nickel-resin affinity column are SEQ ID NO: 31 and SEQ ID NO: 32, respectively.

EXAMPLE 3: PREPARATION OF LIPOSOME AND LIPOSOME/DNA COMPLEX

The PC-PEG-PE liposome was prepared as follows: 5.9 mg of PC (1,2-Dipalmitoyl-sn-Glycero-3Ethylphosphocholine) and 14.6 mg of PEG (1,2-Dipalmitoyl-sn-Glycero-3Phosphoethanolamine-N-Polyethylene glycol-5000), (Avanti Polar Labs, Inc.) were respectively dissolved in 2 ml of solvent (90% chloroform, 10% MeOH) and 1 ml of MeOH, and added into a 500 ml round bottom flask. The flask was rotated on a rotary-evaporator at 55° C. under vacuum after disappearance of liquid. The flask was further vacuum-dried for three cycles of 30 minutes at room temperature and heated for 5 minutes. 6 mg of Polyethylenimine (PE) (Sigma Aldrich) in 6 ml of PBS was added into rotating flask subjected to 5 cycles of 10 minutes of heating and 30 minutes under room temperature. The final solution was adjusted to 6 ml with distilled water and underwent one freeze-thaw procedure (from −20° C. to 4° C.). The solution was passed through a series of filters (1.2, 0.8, 0.45, and 0.22 µm) while keeping at 60° C. water bath to obtain the PC-PEG-PE liposome. The liposome/DNA (e.g., DNA constructs as obtained in Example 1) complexes were freshly prepared within two hours before injection into mice. Liposome was mixed with the DNA stock (1 mg/ml) in equal volumes at room temperature for 20 minutes. The liposome/DNA complex was adjusted to 100 pt with PBS before being administrated to each experimental mouse.

EXAMPLE 4: IMMUNIZATION OF MICE WITH pVAC-1-IL2ss-mCTLA-4, pVAC-1-IL2ss-hCTLA-4, pVAC-1-IL2ss-mCTLA-4-mPD-L1, and pVAC-1-IL2ss-mCTLA-4-mPD-1

C57BL/6 and Balb/c mice aged 6-7 weeks were vaccinated by intramuscular injection with various amounts (ranging from 0, 25, 50 to 100 µg) of pVAC-1-IL2ss-mCTLA-4, pVAC-1-IL2ss-hCTLA-4, and pVAC-1 control vector, as naked DNA or coupled with either one of the two liposome, DOTAP:Chol developed by Nancy-Templeton (Templeton et al., Nat Biotechnol 15, 647-652) or PC-PEG-PE as described above. Immunization was conducted once per week for four weeks.

EXAMPLE 5: DETECTION OF SERUM ANTIBODIES AGAINST CTLA-4, PD-1, AND PD-L1

Figure 2B:
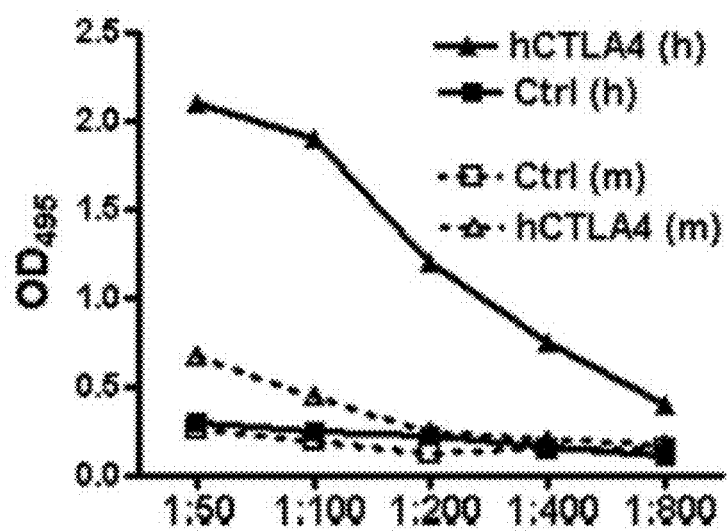
FIG. 2b provides the titer standard curves of the antibody generated by the mice immunized with pVAC-1-IL2ss-hCTLA-4-PLAP, at the dilutions of 1:50, 1:100, 1:200, 1:400, and 1:800.

After the immunization of mice by four weekly intramuscular injection of the aforementioned DNA vaccines, the mice serum was collected and examined for specificity to PD-1, PD-L1 and both human and murine CTLA-4. To detect potential antibody against mCTLA-4, hCTLA-4, mPD-L1 and mPD-1, 96-well EIA plates were prepared by coating with these proteins (R&D systems, Minneapolis, Minn., USA) at 1 µg/ml in borate saline (BS) buffer, pH 8.4, for 4 h at room temperature, and then blocked with borate saline plus 1% (w/v) bovine serum albumin (BS BSA). Serial two-fold dilutions of mouse serum in BSBSA (1:100 to 1:3200) were added to duplicate wells and incubated overnight at 4° C. Plates were washed with PBS with 0.05% (v/v) Tween-20 and incubated with HRP conjugated goat anti-mouse IgG diluted 1:2000 in BSBSA for 2 hours at room temperature. HRP substrate 2,2'-azino-bis(ethylbenzthiazoline sulfonic acid) was added and incubated for 20 min at room temperature. Absorbance was measured at 405 nm on an ELISA reader. In FIG. 2, serum from mice immunized with pVAC-1-IL2ss-hCTLA4-PLAP displayed specific immunity to recombinant human CTLA4 and to a lesser degree to murine CTLA4, whereas, serum from mice immunized with pVAC-1 control vector did not show significant binding activity toward both human and murine CTLA4.

Figure 15A:
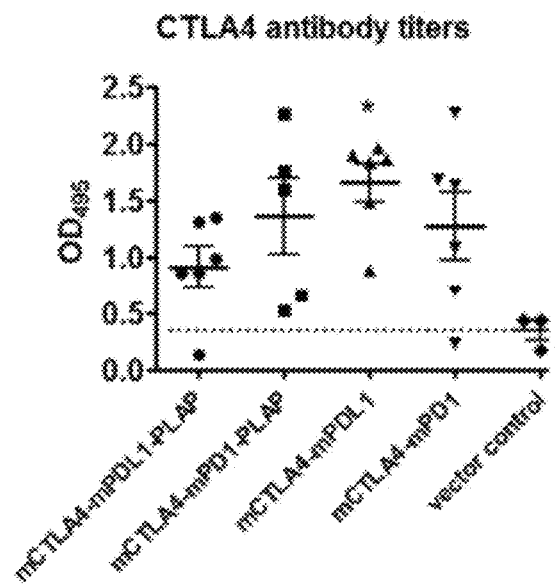
FIGS. 15a and 15b provide the results of the vaccination of mice with pVAC-1-IL2ss-mCTLA4-mPD-L1-PLAP (mCTLA4-mPD-L1-PLAP), pVAC-1-IL2ss-mCTLA4-mPD-1-PLAP (mCTLA4-mPD-1-PLAP), pVAC-1-IL2ss-mCTLA4-mPD-L1 (mCTLA4-mPDL1), pVAC-1-IL2ss-mCTLA4-mPD-1 (mCTLA4-mPD1), and pVAC-1 (vector control)
Figure 15B:
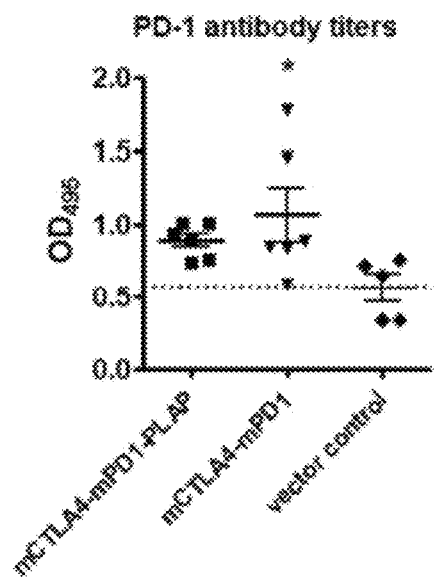
Figure 15C:
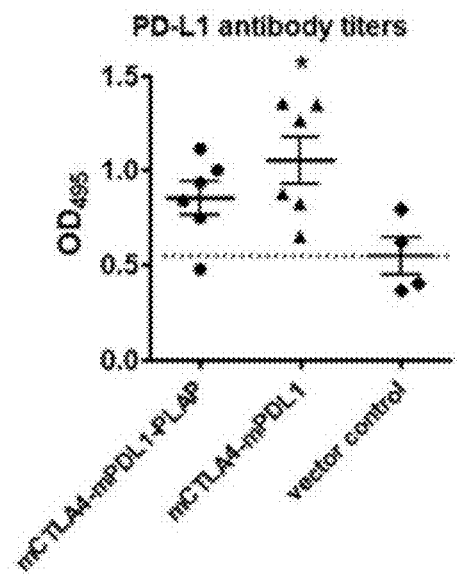
FIG. 15c shows the titers of DNA vaccine induced antibodies against mPD-L1 (PD-L1 antibody titers) as compared with those of the control pVAC-1 vector are shown.

When the experimental mice were immunized with DNA vaccines encoding fusion genes, including mCTLA4-mPD-L1-PLAP, mCTLA4-mPD-L1, mCTLA4-mPD-1-PLAP, or mCTLA4-mPD-1, anti-serum targeting both mCTLA4 and mPD-1, or mCTLA4 and mPD-L1 could be elicited as shown in FIG. 15.

EXAMPLE 6: EFFICACY STUDY OF THE CTIA4 DNA VACCINE

Figure 3:
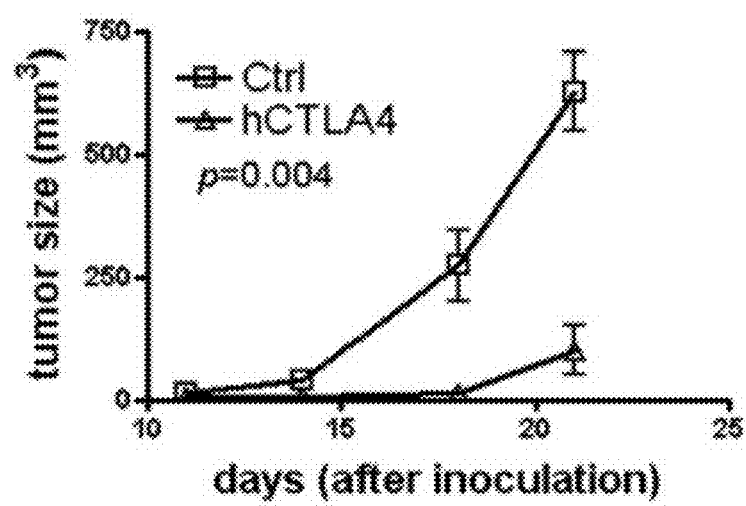
FIG. 3 shows the suppressed growth of B16 melanoma (B16F10 tumor cells) in the mice immunized with pVAC-1-IL2ss-hCTLA-4-PLAP.
Figure 4:
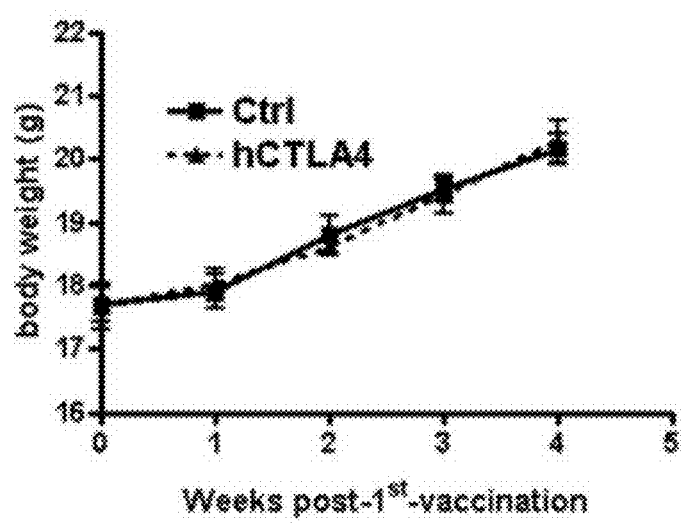
FIG. 4 provides the comparison of the body weights of the mice immunized pVAC-1-IL2ss-hCTLA-4 with those of the control group treated with pVAC-1 vector, which shows no difference between the two groups.

Melanoma cells (B16F10) were used for efficacy study of the DNA vaccines of the present invention. To examine the protective effect of immunity against CTLA-4, the c57/BL mice immunized with pVAC-1-IL2ss-hCTLA-4-PLAP ("hCTLA4") of the invention were inoculated with B16F10 melanoma cells. As shown in FIG. 3, the B16F10 tumor growth rate in the hCTLA4 vaccinated mice was significantly slower than that of mice treated with the control pVAC-1 vector (p=0.004). Although the hCTLA4 vaccinated mice obtained immune response against CTLA-4 sufficient for inhibition of tumor growth, they did not show any sign of colitis, which is the most common side effect occurred in cancer patients enrolled in anti-CTLA-4 monoclonal antibody trial (Di Giacomo et al., Cancer Immunol Immunother 58(8):1297-306). The mice did not show discernible difference in body weight gains during a period of five weeks while being treated with either the pVAC-1-IL2ss-hCTLA-4-PLAP DNA vaccine or the control pVAC-1 vector (see FIG. 4).

EXAMPLE 7: ASSAY OF CYTOTOXICITY ON CANCER CELLS

Figure 5A:
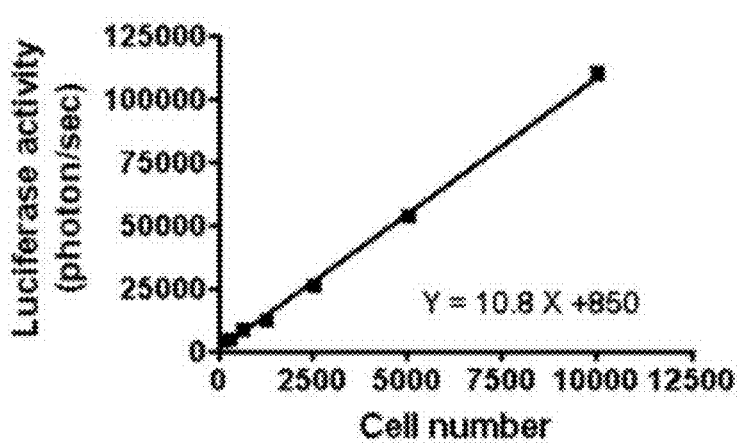
FIG. 5a provides the correlation between the numbers of B16F10 cell stably expressing luciferase (B16F10-luc) and luciferase activity.
Figure 5B:
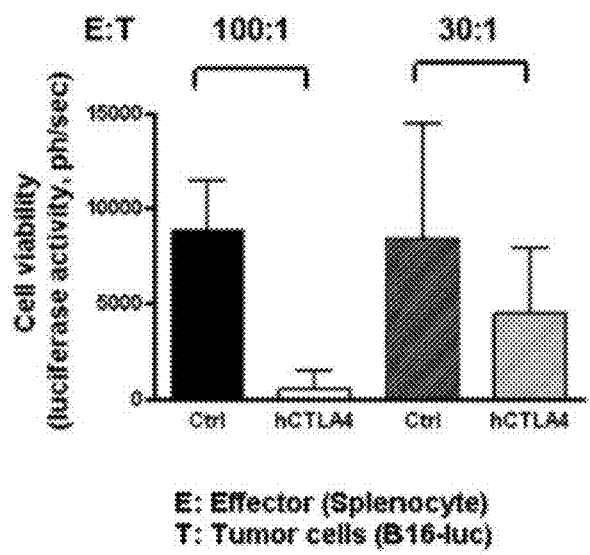
FIG. 5b provided the enhanced cytotoxicity, shown as decreased B16F10-luc cell viability, of splenocytes from mice immunized with pVAC-1-IL2ss-hCTLA-4-PLAP at the ratios of Effector (splenocytes): Tumor cells (B16F10-luc) of 100:1 and 30:1.

To characterize the mechanisms of anticancer effect of pVAC-1-IL2ss-CTLA-4-PLAP vaccine, the immunized mice were sacrificed and the splenocytes were collected for examination of cytotoxic effect on cancer cells. The splenocyte-mediated cytotoxicity was measured using the previously screened B16F10 cells stably expressing luciferase (B16F10-luc cells), of which the cell numbers demonstrated good correlation with luciferase activity represented as photon counts per second (see FIG. 5a). The B16F10-luc cells (2000 cells/well) were added into 96-well in the presence of 100- or 30-fold ($2 \times 10^5$ or $6 \times 10^4$ cells) of splenocytes. One day after incubation, the cells were added with luciferase substrate, luciforin, and subjected to IVIS Imaging System for quantification of cell viability represented by photon counts per second. The splenocytes from mice immunized with pVAC-1-IL2ss-hCTLA-4 demonstrated superior effects on cell viability of B16F10 (see FIG. 5b).

EXAMPLE 8: INTERFERON-GAMMA MEASUREMENT

Figure 6:
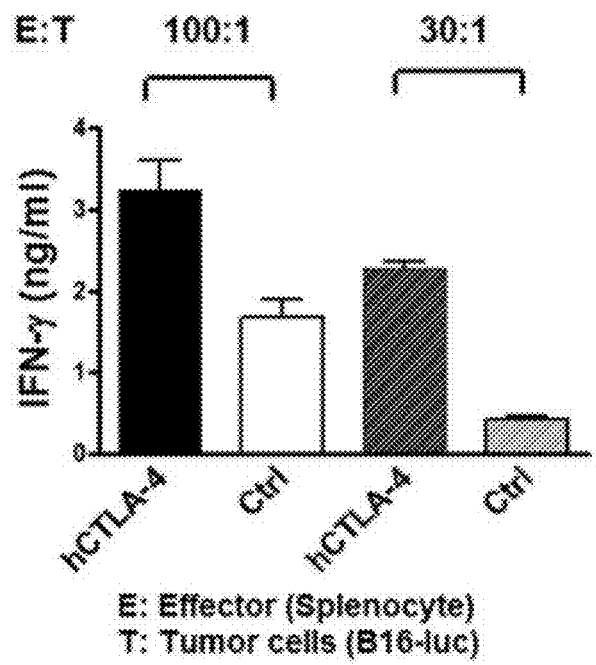
FIG. 6 provides the enhanced B16F10-luc-stimulated secretion of interferon-gamma by splenocytes from the mice immunized with pVAC-1-IL2ss-hCTLA-4-PLAP.

To characterize the immune response of splenocytes encountering B16F10-luc, the amount of interferon-gamma as produced were measured. The splenocytes obtained from the immunized mice were incubated with the CTLA4 antigen and the stimulated secretions of interferon-gamma were measured using an ELISA kit (R&D system) specific for interferon-gamma. Similarly, the splenocytes from the tumor-bearing mice vaccinated with either control pVAC-1 or pVAC-1-IL2ss-CTLA-4-PLAP of the present invention were stimulated with corresponding tumor cells and secretion of interferon-gamma was evaluated accordingly. The splenocytes obtained from the pVAC-1-IL2ss-CTLA-4-PLAP immunized mice produced higher amount of interferon-gamma as compared with those from pVAC-1 vaccinated control mice (see FIG. 6).

EXAMPLE 9: EFFICACY STUDY OF LIPOSOME COUPLED DNA VACCINE

Figure 7A:
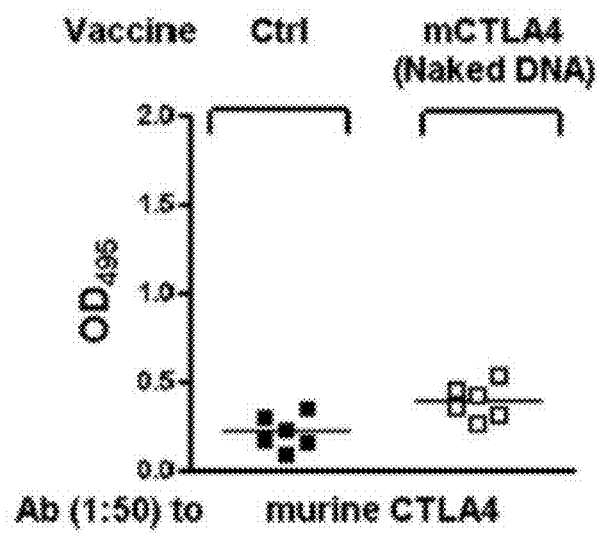
FIG. 7a provides the vaccination of mice with pVAC-1-mCTLA-4-PLAP without coupling to cationic liposome (as "naked DNA"), which shows that no significant titer of antibody against murine CTLA-4 was induced in murine serum at 1:50 dilution.
Figure 7B:
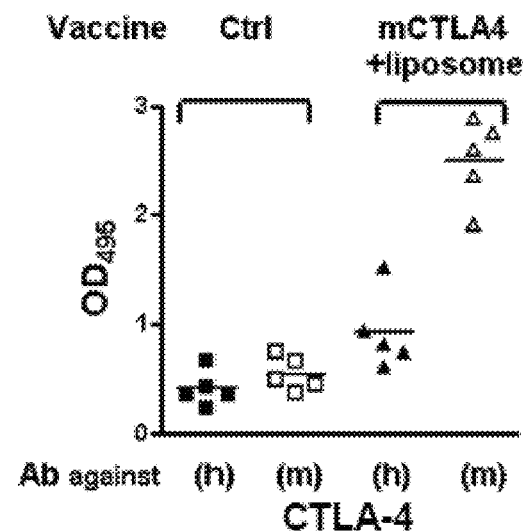
FIG. 7b and FIG. 7c provide the results of the vaccination of mice with pVAC-1-mCTLA-4-PLAP coupled with liposome generating antibodies against both human and murine CTLA-4 as compared with the mice with the naked DNA control.
Figure 7C:
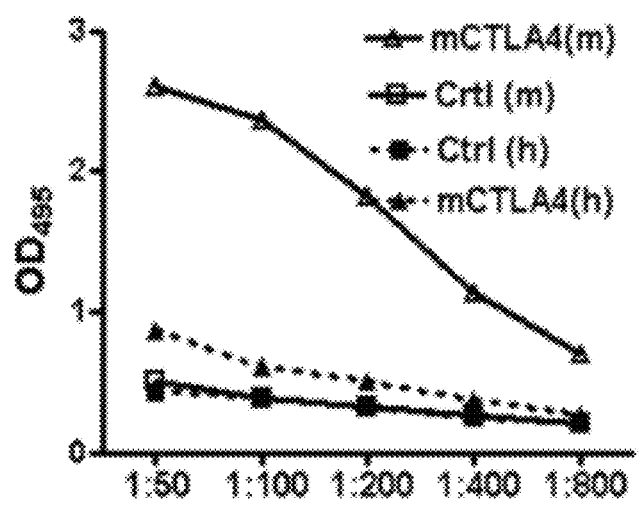
Figure 8:
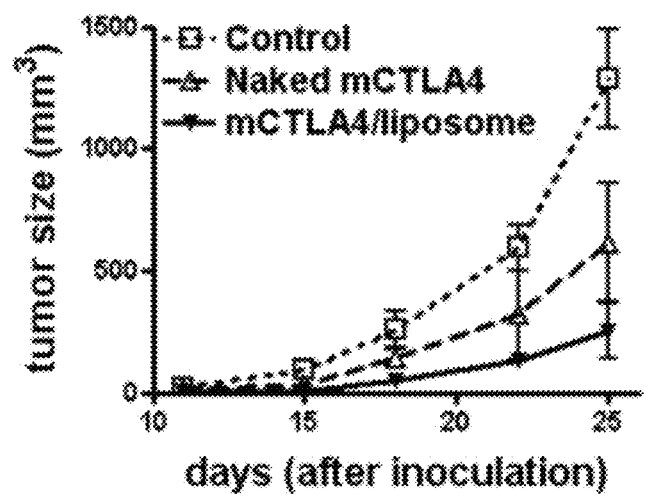
FIG. 8 provides the results of the vaccination of mice with the pVAC-1-mCTLA-4 DNA-liposome complex which suppressed RENCA tumor growth.

Murine renal cell carcinoma (RENCA) was also used for efficacy study. An animal experiment involving a renal cell carcinoma model in balb/c mice was conducted. The mice were immunized with pVAC-1-mCTLA-4-PLAP to induce antibody in mice more specific to autogenic antigen. In the absence of coupling cationic liposome, the "naked" pVAC-1-mCTLA-4 DNA vaccine failed to arouse significant antibody titers (see FIG. 7a) targeting mCTLA-4. Given that cationic liposome coupling to the DNA vaccine as prepared in Example 3 increased transfection efficiency as well as enhanced immune response, the pVAC-1-mCTLA-4-liposome complex for the induction of immune response against murine CTLA-4 was investigated to provide a better form of the DNA vaccines. This approach substantially elicited antibody titer against murine CTLA-4 and to a lesser degree against human CTLA-4 (FIG. 7 b and c). The mice immunized with the pVAC-1-mCTLA-4-liposome complex also demonstrated an inhibited growth of the renal cell carcinoma (RENCA) as compared with those immunized with the control pVAC-1 DNA vaccine, or the naked pVAC-1-mCTLA-4 DNA vaccine only (see FIG. 8, the pVAC-1-mCTLA4-liposome complex versus the control DNA vaccines: p<0.01).

EXAMPLE 10: FLOW CYTOMETRY ANALYSIS

Figure 9:
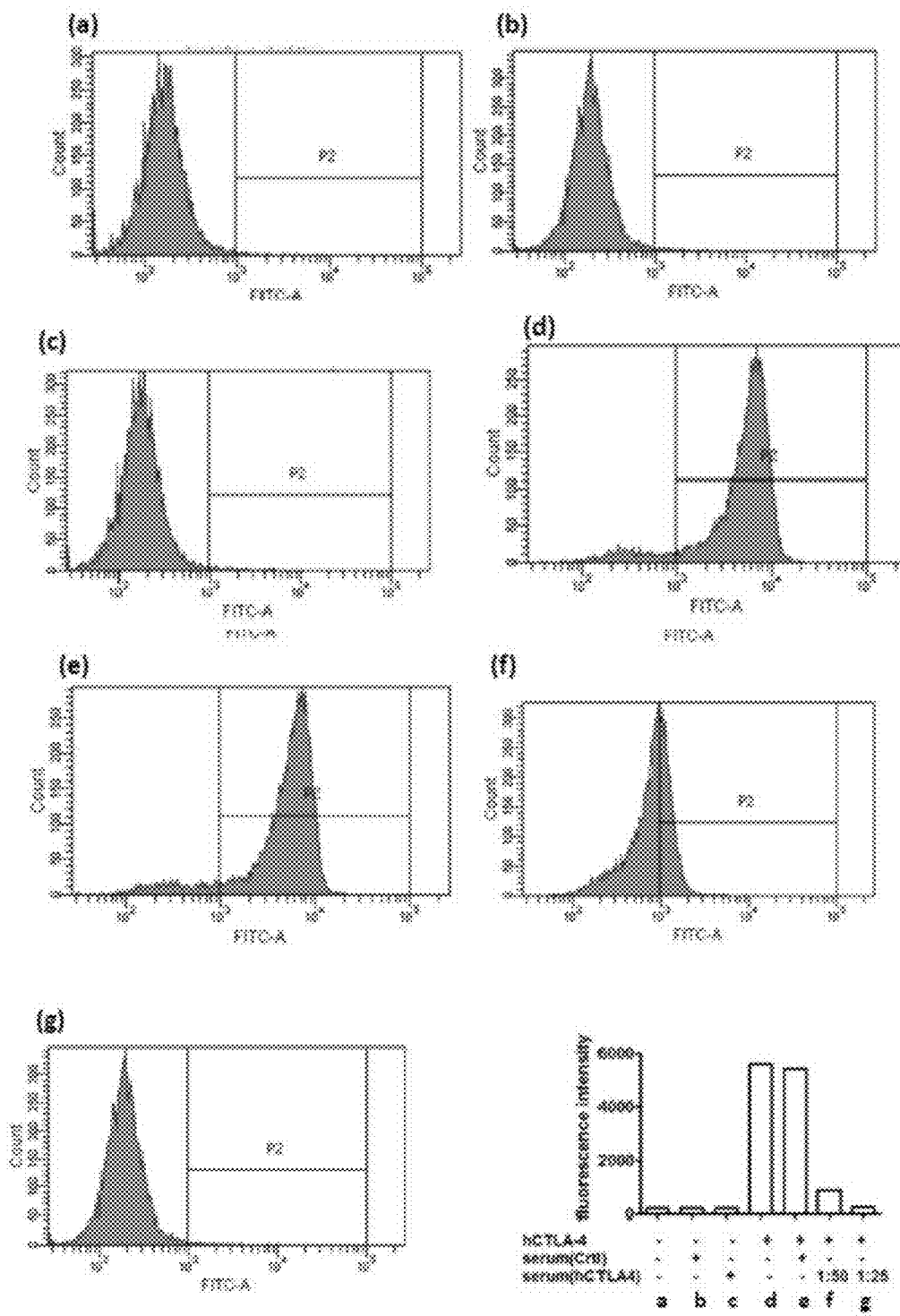
FIG. 9 provides the interactions between purified hCTLA-4 and its receptors B7.1 and B7.2, stably expressed on CHO-B7.1 and CHO-B7.2, respectively. The interactions were inhibited by the serum of the mice immunized with pVAC-1-IL2ss-hCTLA-4-PLAP.

Given that CTLA-4 exerts its function by binding to CD-80 (B7.1) and CD-86 (B7.2) on the surface of antigen-presenting cells, the inhibitory effect of serum of mice on interaction between purified hexa-histidine ($His_6$) tagged CTLA-4 protein and B7.1 and B7.2 stably expressed on Chinese hamster ovarian (CHO) cells were examined. B7-1 or B7-2 stably expressing CHO cells were provided by Dr. M. H. Tao at Academia Sinica, Taipei, Taiwan. The cells ($5 \times 10^5$) were incubated with 2 ng/ml of hexa-histidine tagged human CTLA in the presence or absence of serum of mice immunized with the pVAC-1-IL2ss-hCTLA-4 DNA vaccine or the control DNA vaccine at 4° C. for 30 minutes. The bound proteins were detected with FITC-labeled mouse anti-his6 Ab at 1:200 and subjected to FACS analysis. The results were shown in FIG. 9. It was indicated that the interaction between $His_6$-human CTLA-4 (2 ng/ml) and B7.1/B7.2 expressed on stably transfected CHO cells ($5 \times 10^5$ cells/assay) was blocked by the serum obtained from the mice immunized with the pVAC-1-IL2ss-hCTLA-4-PLAP DNA vaccine, whereas no sign of inhibition were found in those from the control group at 1:25 dilution (see FIG. 9).

EXAMPLE 11: ADDITIONAL STUDY FOR DNA VACCINES AGAINST CTLA-4, PD-1 AND PD-L1

In addition to the promising result of the pVAC-1-IL2ss-CTLA-4-PLAP DNA vaccine, other DNA vaccines targeting multiple immune-suppressing proteins, including CTLA-4 and PD-1 or PD-L1, were constructed (FIGS. 11 and 12) and investigated for efficacy, which were based on pVAC-1 vector similar to pVAC-1-IL2ss-CTLA-4-PLAP. According to the present invention, these vaccines include:
pVAC1-IL2ss hPD-1-PLAP (SEQ ID NO: 3);
pVAC1-IL2ss hPD-1 (SEQ ID NO: 4);

pVAC1-IL2ss hPD-L1-PLAP (SEQ ID NO: 5);
pVAC1-IL2ss hPD-L1 (SEQ ID NO: 6);
pVAC1-IL2ss hCTLA4-hPD-1-PLAP (SEQ ID NO: 7);
pVAC1-IL2ss hCTLA4-hPD-1 (SEQ ID NO: 8);
pVAC1-IL2ss hCTLA4-hPD-L1-PLAP (SEQ ID NO: 9);
pVAC1-IL2ss hCTLA4-hPD-L1 (SEQ ID NO: 10);
pVAC1-IL2ss mPD-1-PLAP (SEQ ID NO: 11);
pVAC1-IL2ss mPD-1 (SEQ ID NO: 12);
pVAC1-IL2ss mPD-L1-PLAP (SEQ ID NO: 13);
pVAC1-IL2ss mPD-L1 (SEQ ID NO: 14);
pVAC1-IL2ss mCTLA4-mPD-1-PLAP (SEQ ID NO: 15);
pVAC1-IL2ss mCTLA4-mPD-1 (SEQ ID NO: 16);
pVAC1-IL2ss mCTLA4-mPD-L1-PLAP (SEQ ID NO: 17); and
pVAC1-IL2ss mCTLA4-mPD-L1 (SEQ ID NO: 18);
wherein the IL2 signal peptide ("IL2ss") (SEQ ID NO: 19) was used as the signal peptide, which contains 21 amino acids and shares common characteristics with signal peptides of other secretory proteins with respect to abundance and positions of hydrophobic amino acids; the intracellular cleavage of the IL2ss occurs after Ser20 and leads to the secretion of the antigenic protein; the Restriction site was BamHI or EcoRI; a hydrophobic COOH-terminal sequence of 32 residues ("PLAP" derived from placental alkaline phosphatase), which serves as a transmembrane domain to tether the translated protein to cell membrane (SEQ ID NO: 20); the sequence targeting hCTLA4 is the DNA sequence coding for the amino acid sequence at the 37th-160th residues of hCTLA4 (SEQ ID NO: 21); and the sequence targeting mCTLA4 is the DNA sequence coding for the amino acid sequence at the 36th-161st residues of mCTLA4 (SEQ ID NO: 22); the sequence targeting hPD-1 is the DNA sequence coding for the amino acid sequence at the 21st-170th residues of hPD-1 (SEQ ID NO: 23); the sequence targeting mPD-1 is the DNA sequence coding for the amino acid sequence at the 21st-170th residues of mPD-1 (SEQ ID NO: 24); the sequence targeting hPDL-1 is the DNA sequence coding for the amino acid sequence at the 19th-238th residues of hPD-L1 (SEQ ID NO: 25); the sequence targeting mPD-L1 is the 19th-127th residues of mPD-L1 (SEQ ID NO: 26); the sequence targeting both hCTLA4 and hPD-1 is the DNA sequence coding for the amino acid sequence at the 37th-160th residues of hCTLA4 and the amino acid sequence at the 21st-170th residues of hPD-1 (hCTLA4-hPD-1) (SEQ ID NO: 27); the sequence targeting both hCTLA4 and hPD-L1 is the DNA sequence coding for the amino acid sequence at the 37th-160th residues of hCTLA4 and the amino acid sequence at the 19th-238th residues of PD-L1 (hCTLA4-hPD-L1) (SEQ ID NO: 28); the sequence targeting both mCTLA4 and mPD-1 is the DNA sequence coding for the amino acid sequence at the 36th-161st residues of mCTLA4 and the amino acid sequence at the 21st-170th residues of mPD-1 (mCTLA4-mPD-1) (SEQ ID NO: 29); and the sequence targeting both mCTLA4 and mPD-L1 is the DNA sequence coding for the amino acid sequence at the 36th-161st residues of mCTLA4 and the amino acid sequence at the 19th-127th residues of mPD-L1(mCTLA4-mPD-L1) (SEQ ID NO: 30).

According to the present invention, other DNA vaccines targeting more than two immune-suppressing proteins can be constructed, such as pVAC1-IL2ss-CTLA4-PD1-PDL1. Some of the embodiments are shown in FIG. 13 and below:
(1) pVAC1-IL2ss-hCTLA4-hPD1-hPDL1 (SEQ ID NO: 33 or SEQ ID NO: 34); and
(2) pVAC1-IL2ss-mCTLA4-mPD1-mPDL1 (SEQ ID NO: 35 or SEQ ID NO: 36);

wherein the sequence targeting hCTLA4, hPD-1 and hPD-L1 is the DNA sequence coding for the amino acid sequence at the 37th-160th residues of hCTLA4, the amino acid sequence at the 31st-147th residues of hPD-1 and the amino acid sequence at the 19th-127th or 19th-238th residues of hPD-L1 (hCTLA4-hPD-1-hPD-L1); and the sequence targeting mCTLA4, mPD-1 and mPD-L1 is the DNA sequence coding for the amino acid sequence at the 36th-161st residues of mCTLA4, the amino acid sequence at the 31st-147th residues of mPD-1, and the amino acid sequence at the 19th-127th or 19th-237th residues of mPD-L1 (mCTLA4-mPD-1-mPD-L1).

Figure 14A:
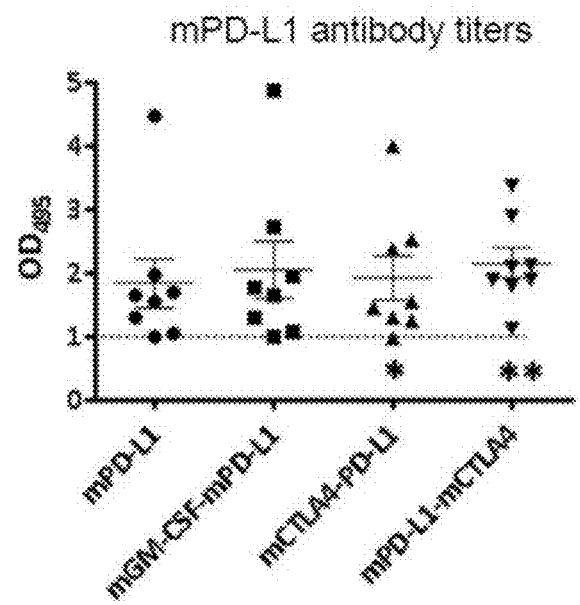
FIGS. 14a and 14b provide the results of the vaccination of mice with pVAC-1-IL2ss-mPD-L1-PLAP (mPD-L1), pVAC-1-IL2ss-GM-CSF-mPD-L1-PLAP (mGM-CSF-mPD-L1), pVAC-1-IL2ss-mCTLA4-mPD-L1-PLAP (mCTLA4-PD-L1), pVAC-1-IL2ss-mPD-L1-mCTLA4-PLAP (mPD-L1-mCTLA4), and pVAC-1 (control vector).
Figure 14B:
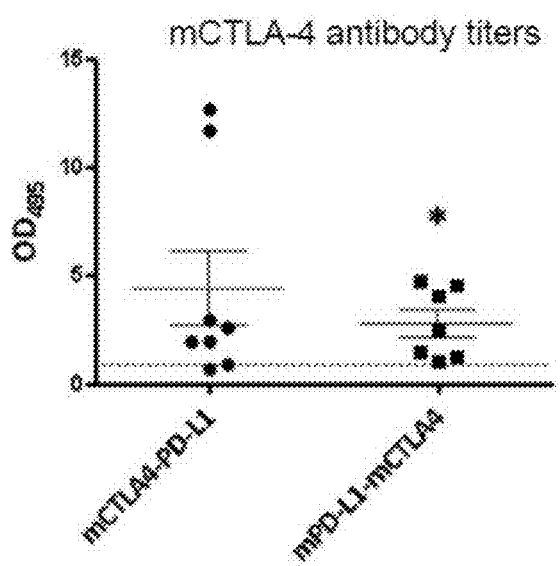

The immunity against these antigens was investigated using similar vaccination protocol as that adopted in the pVAC-1-IL2ss-CTLA4-PLAP DNA vaccine shown in the previous examples. The positive results for these constructs were obtained, which demonstrated simultaneous enhancement of immunity in terms of the efficacy in increasing antibody titers against murine CTLA-4 as well as PD-L1 by immunizing the mice with either pVAC-1-IL2ss-mCTLA4-PD-L1-PLAP or pVAC-1-IL2ss-mPD-L1-CTLA-4-PLAP (FIG. 14). As shown in FIG. 14, the dotted line represents the antibody titer of the serum from the control group injected with the control pVAC-1 vector, whereas those of the serum from the mice injected with the DNA vaccines as mentioned above were normalized to the data of control mice (vaccine groups vs. control: *=$p<0.05$, **=$p<0.01$)

EXAMPLE 12: IMMUNIZATION OF MICE WITH PVAC-1-IL2SS-MCTLA-4-MPD-L1-PLAP, PVAC-1-IL2 SS-MCTLA-4-MPD-L1, PVAC-1-IL2 SS-MCTLA-4-MPD-1-PLAP, PVAC-1-IL2 SS-MCTLA-4-MPD-1, OR PVAC-1 CONTROL VECTOR

Balb/c mice of 6-7 weeks old were vaccinated by intramuscular injection once per week for three weeks with 70 μg of pVAC-1-IL2ss-mCTLA-4-mPD-L1-PLAP, pVAC-1-IL2ss-mCTLA-4-mPD-L1, pVAC-1-IL2ss-mCTLA-4-mPD-1-PLAP, pVAC-1-IL2ss-mCTLA-4-mPD-1, or pVAC-1 DNA vaccines. The fourth immunization was conducted with the same amount of DNA vaccines except that electroporation was applied immediately with voltage of 2 pulses, 1,000 V/cm after intramuscular injection of DNA using two needle electrodes placed to flank the injection area. The induced antiserum against CTLA4, PD-1 and PD-L1 was detected as described in Example 5. The serum from mice immunized with pVAC-1-IL2ss-mCTLA-4-mPD-L1-PLAP, pVAC-1-IL2ss-mCTLA-4-mPD-L1, pVAC-1-IL2ss-mCTLA-4-mPD-1-PLAP, and pVAC-1-IL2ss-mCTLA-4-mPD-1 all displayed increased antibody titer against CTLA4 as compared with that from pVAC-1 (vector control) immunized mice (pVAC-1-IL2ss-mCTLA-4-mPD-L1 vs. pVAC-1: $p<0.05$, FIG. 15a). Moreover, the serum from mice immunized with pVAC-1-IL2ss-mCTLA-4-mPD-1-PLAP, pVAC-1-IL2ss-mCTLA-4-mPD-1, and those immunized with pVAC-1-IL2ss-mCTLA-4-mPD-L1-PLAP and pVAC-1-IL2ss-mCTLA-4-mPD-L1 demonstrated antibody titers against PD-1 (FIG. 15b) and PD-L1 (FIG. 15c), respectively, as compared with the serum from pVAC-1 immunized mice.

EXAMPLE 13: IMMUNIZATION WITH FUSION DNA CONSTRUCTS PROVIDES PROTECTIVE EFFECTS AGAINST RENAL CELL CARCINOMA IN MICE

Figure 16:
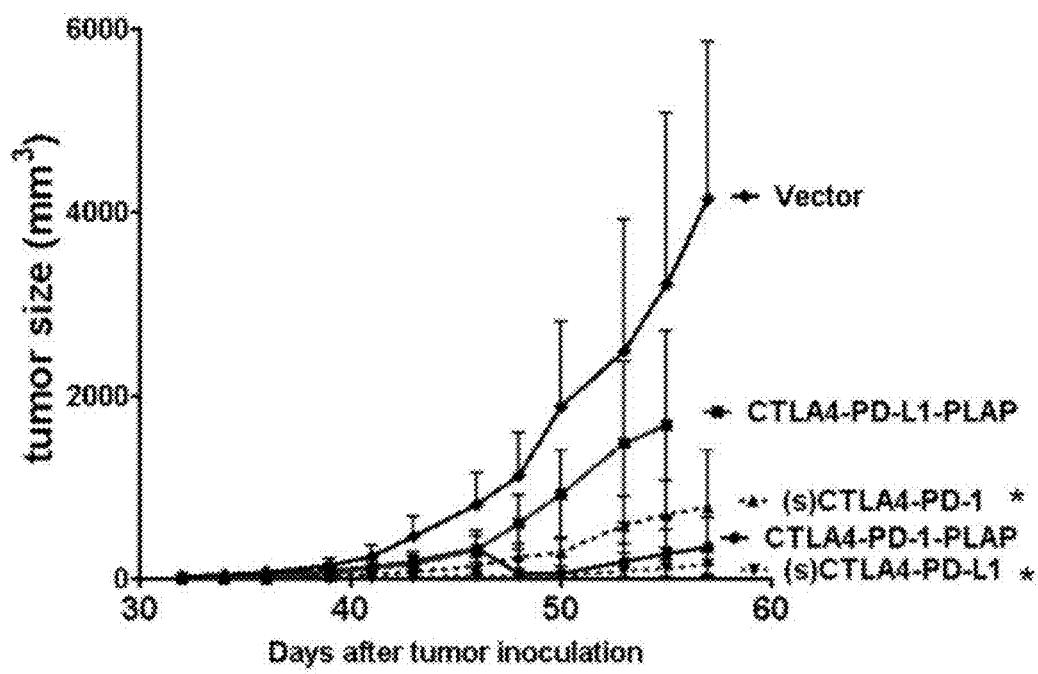
FIG. 16 provides the results of the vaccination of the mice with pVAC-1-IL2ss-mCTLA4-mPD-L1-PLAP (CTLA4-PD-L1-PLAP), p VAC-1-IL2ss-mCTLA4-mPD-1-PLAP (CTLA4-PD-1-PLAP), pVAC-1-IL2ss-mCTLA4-mPD-L1 ((s)CTLA4-PD-L1), and pVAC-1-IL2ss-mCTLA4-mPD-1 ((s)CTLA4-PD-L1) which suppressed RENCA tumor growth.
Figure 17:
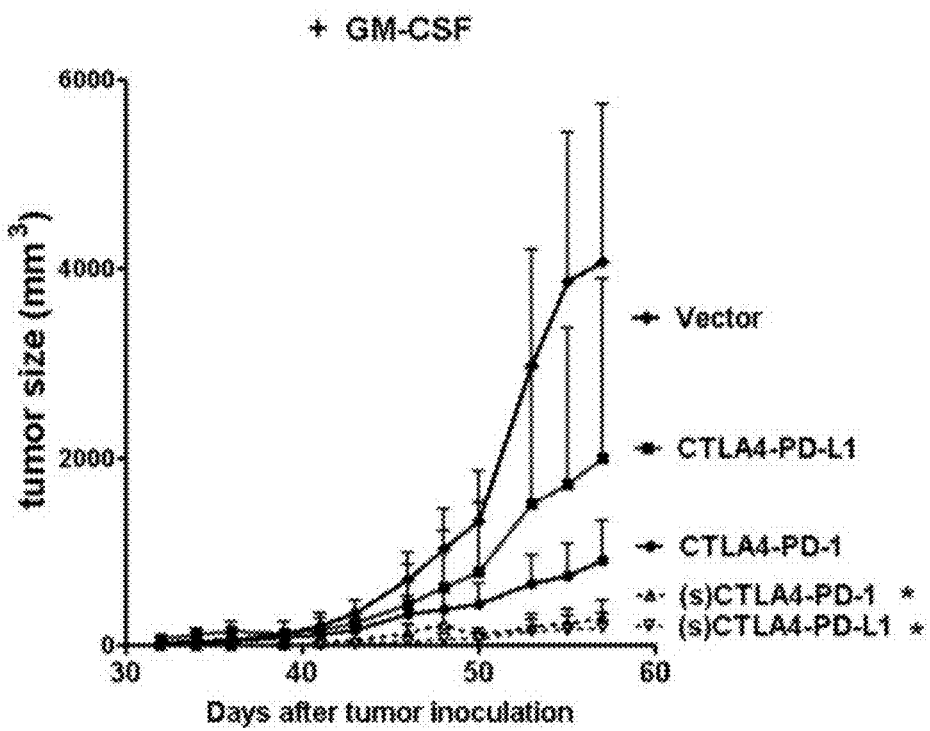
FIG. 17 provides the results of the vaccination of the mice with pVAC-1-IL2ss-mCTLA4-mPD-L1-PLAP (CTLA4-PD-L1), pVAC-1-IL2ss-mCTLA4-mPD-1-PLAP (CTLA4-PD-1), pVAC-1-IL2ss-mCTLA4-mPD-L1 ((s)CTLA4-PD-L1), and pVAC-1-IL2ss-mCTLA4-mPD-1 ((s)CTLA4-PD-1) in combination of GM-CSF DNA which suppressed RENCA tumor growth.
Figure 18:
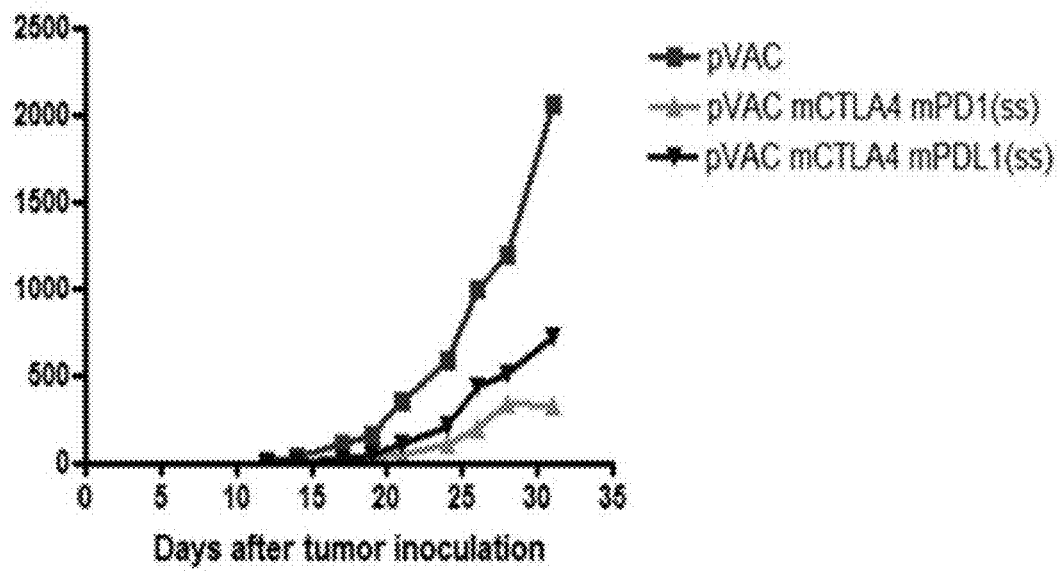
FIG. 18 provides the results of the vaccination of the mice with pVAC-1-IL2ss-mCTLA4-mPD-L1 (pVAC mCTLA4 mPDL1(ss)) and pVAC-1-IL2ss-mCTLA4-mPD-1 (pVAC mCTLA4 mPD1(ss)) which suppressed CT26 tumor growth.

The mice were immunized with pVAC-1-IL2ss-mCTLA-4-mPD-L1-PLAP, pVAC-1-IL2ss-mCTLA-4-mPD-L1, pVAC-1-IL2ss-mCTLA-4-mPD-1-PLAP, pVAC-1-IL2ss-mCTLA-4-mPD-1, or pVAC-1 DNA vaccines in the presence of co-administration of 30 µg of either pORF-GM-CSF (as a vaccine adjuvant) or pORF vector (control). They were subjected to four weekly intramuscular injections of the DNA. The last injection in the fourth week was followed by immediate electroporation applied to the injection sites as described in Example 12. One week after the last vaccination, the mice were subcutaneously inoculated with murine renal cell carcinoma, RENCA (2×10⁴ cells/mouse). As shown in FIGS. 16 and 17, mice immunized with fusion DNA vaccines, especially pVAC-1-IL2ss-mCTLA4-mPD-L1 and pVAC-1-IL2ss-mCTLA4-mPD-1, demonstrated most significantly suppressed tumor growth as compared with those immunized with pVAC-1 vector control (immunization with (FIG. 17) or without (FIG. 16) co-administration of GM-CSF DNA). Similarly, mice immunized with pVAC-1-IL2ss-mCTLA4-mPD-L1 and pVAC-1-IL2ss-mCTLA4-mPD-1 displayed suppressed CT26 tumor growth as compared with those mice immunized with pVAC-1 control DNA (FIG. 18).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for enhancing immune response in a subject under the treatment of an infectious or malignant disease, comprising administering the subject topically, subcutaneously or intramuscularly with a pharmaceutical composition comprising a DNA construct fused with a mammalian expression vector and a pharmaceutically acceptable carrier, wherein the DNA construct comprises (1) a polynucleotide sequence encoding Cytotoxic T-lymphocyte antigen-4 (CTLA-4) or a fragment thereof, and (2) programmed death-1 (PD-1) or a fragment thereof.

2. The method of claim 1, wherein the subject is treated with an anti-infection or anti-cancer drug causing a stimulation of immune response in the subject.

3. The method of claim 1, wherein the subject is under the treatment of a malignant disease.

4. The method of claim 1, wherein the malignant disease is selected from the group consisting of metastatic melanoma, pancreatic cancer, colorectal cancer, hepatocellular carcinoma, lymphoma, hormone refractory prostate cancer, ovarian cancer, acute myeloid leukemia, and non-small cell lung cancer.

* * * * *